(12) United States Patent
Hareyama et al.

(10) Patent No.: US 9,808,305 B2
(45) Date of Patent: Nov. 7, 2017

(54) ENERGY TREATMENT APPARATUS

(71) Applicant: OLYMPUS CORPORATION, Hachioji-shi, Tokyo (JP)

(72) Inventors: Norihiko Hareyama, Hino (JP); Akinori Kabaya, Berlin (DE)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/371,446

(22) Filed: Dec. 7, 2016

(65) Prior Publication Data
US 2017/0079707 A1 Mar. 23, 2017

Related U.S. Application Data

(63) Continuation of application No. PCT/JP2015/077319, filed on Sep. 28, 2015.

(30) Foreign Application Priority Data

Oct. 31, 2014 (JP) .................................. 2014-223527

(51) Int. Cl.
*A61B 18/10* (2006.01)
*A61B 17/32* (2006.01)
(Continued)

(52) U.S. Cl.
CPC ...... *A61B 18/10* (2013.01); *A61B 17/320068* (2013.01); *A61B 17/320092* (2013.01);
(Continued)

(58) Field of Classification Search
CPC .... A61B 17/320068; A61B 17/320092; A61B 18/08; A61B 18/082; A61B 18/085;
(Continued)

(56) References Cited

U.S. PATENT DOCUMENTS

2014/0005703 A1* 1/2014 Stulen .................... A61B 17/29
606/169

FOREIGN PATENT DOCUMENTS

JP   H03-131245 A   6/1991
JP   H03-151957 A   6/1991
(Continued)

OTHER PUBLICATIONS

Yates David C, Translated JP2009189838A, Aug. 27, 2009.*
(Continued)

*Primary Examiner* — Ronald Hupczey, Jr.
*Assistant Examiner* — Tigist Demie
(74) *Attorney, Agent, or Firm* — Oliff PLC

(57) ABSTRACT

In an energy treatment apparatus, maximum source electric power of source electric power output from an electric power source is defined, first energy is generated by supplying first driving electric power to a first energy generator due to the source electric power, and second energy is generated by supplying second driving electric power to a second energy generator due to the source electric power. A controller keep the sum of the first driving electric power and the second driving electric power that are supplied per unit time less than or equal to the maximum source electric power of the electric power source continuously with time.

15 Claims, 18 Drawing Sheets

(51) Int. Cl.
  *A61B 18/08* (2006.01)
  *A61B 18/12* (2006.01)
  *A61B 18/14* (2006.01)
  *A61B 17/00* (2006.01)
  *A61B 18/00* (2006.01)
  *A61B 17/29* (2006.01)

(52) U.S. Cl.
  CPC ............ *A61B 18/08* (2013.01); *A61B 18/082* (2013.01); *A61B 18/085* (2013.01); *A61B 18/1206* (2013.01); *A61B 18/1445* (2013.01); A61B 2017/00026 (2013.01); A61B 2017/00084 (2013.01); A61B 2017/00106 (2013.01); A61B 2017/00734 (2013.01); A61B 2017/2929 (2013.01); A61B 2018/0072 (2013.01); A61B 2018/00077 (2013.01); A61B 2018/00589 (2013.01); A61B 2018/00607 (2013.01); A61B 2018/00678 (2013.01); A61B 2018/00702 (2013.01); A61B 2018/00708 (2013.01); A61B 2018/00767 (2013.01); A61B 2018/00779 (2013.01); A61B 2018/00791 (2013.01); A61B 2018/00875 (2013.01); A61B 2018/00988 (2013.01); A61B 2018/00994 (2013.01)

(58) Field of Classification Search
  CPC . A61B 18/10; A61B 18/1206; A61B 18/1445; A61B 2017/00026; A61B 2017/00084; A61B 2017/00106; A61B 2017/00734; A61B 2017/02
  See application file for complete search history.

(56) References Cited

FOREIGN PATENT DOCUMENTS

| | | | |
|---|---|---|---|
| JP | 2009-189838 A | | 8/2009 |
| JP | 2009189838 A | * | 8/2009 |
| JP | 2009-247893 A | | 10/2009 |
| JP | 2012-096045 A | | 5/2012 |
| JP | 2013-154167 A | | 8/2013 |
| WO | 2010/064530 A1 | | 6/2010 |

OTHER PUBLICATIONS

Dec. 22, 2015 International Search Report issued in International Patent Application No. PCT/JP2015/077319.

May 2, 2017 International Preliminary Report on Patentability issued in International Patent Application No. PCT/JP2015/077319.

* cited by examiner

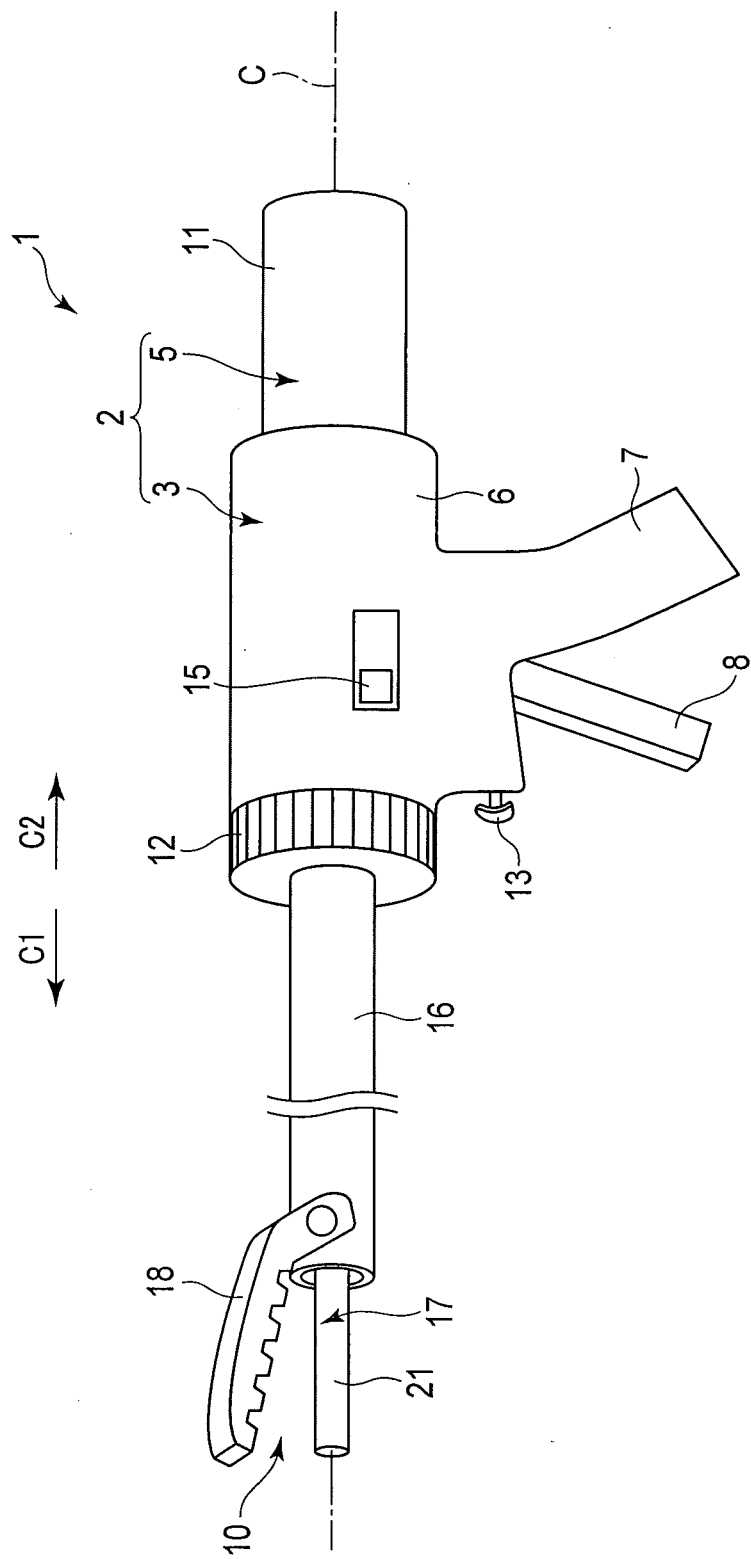
F I G. 1

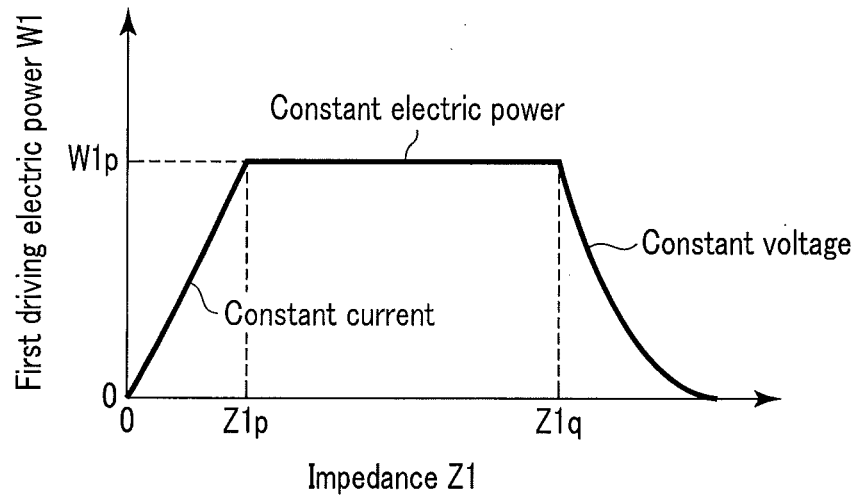
F I G. 4
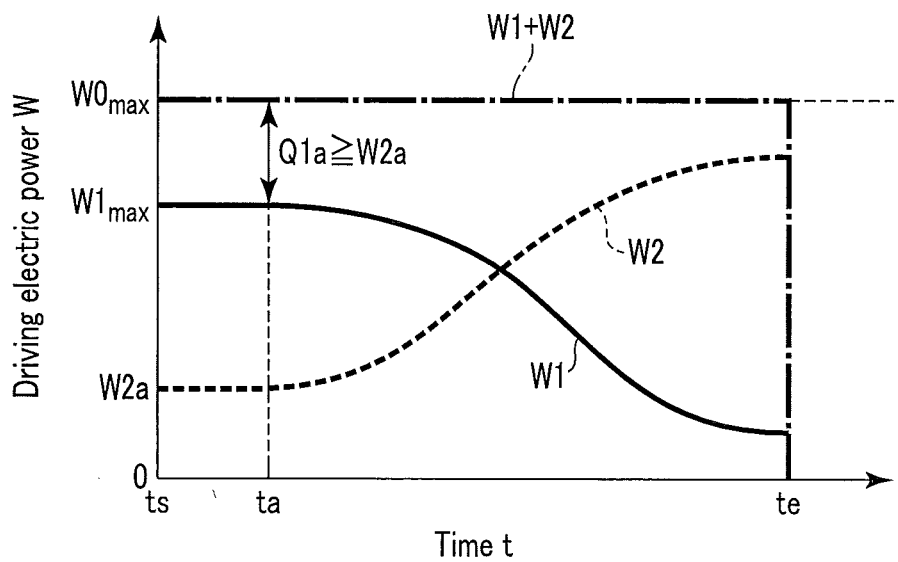
F I G. 5

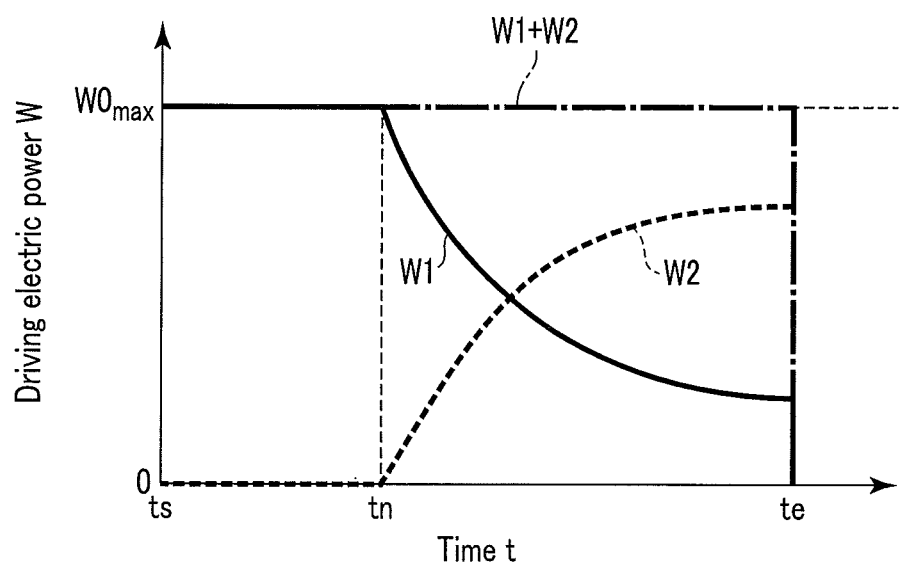
F I G. 13

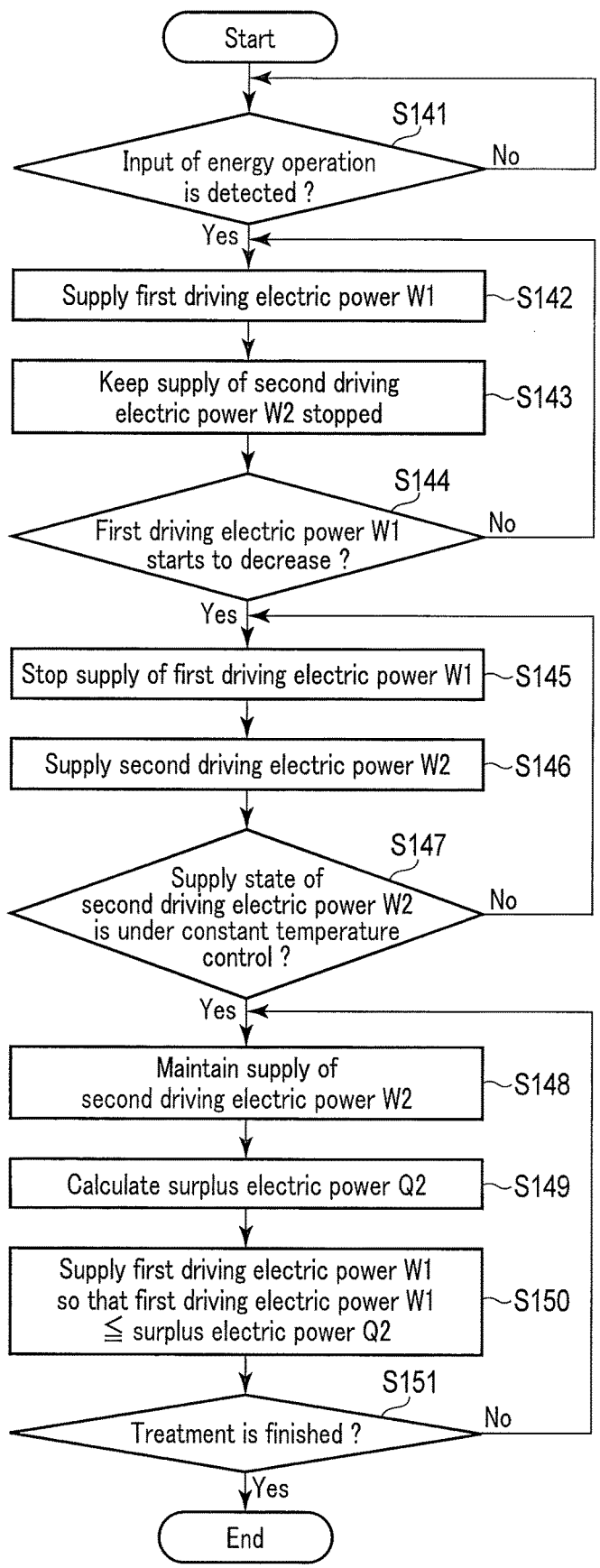
F I G. 14

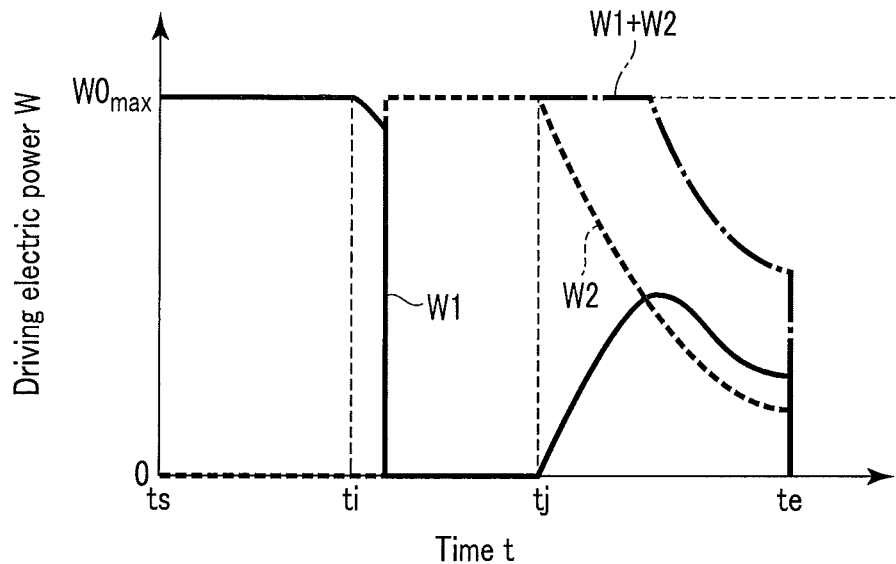
F I G. 15
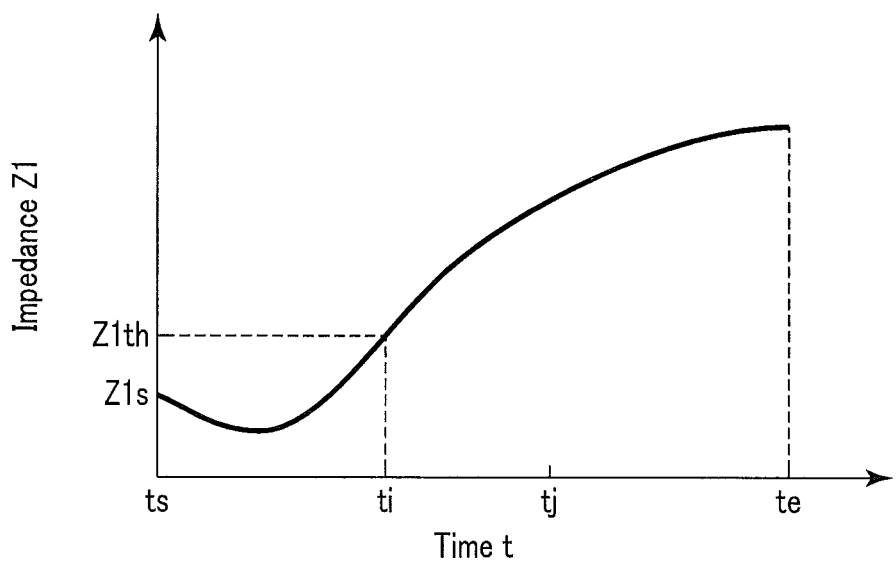
F I G. 16

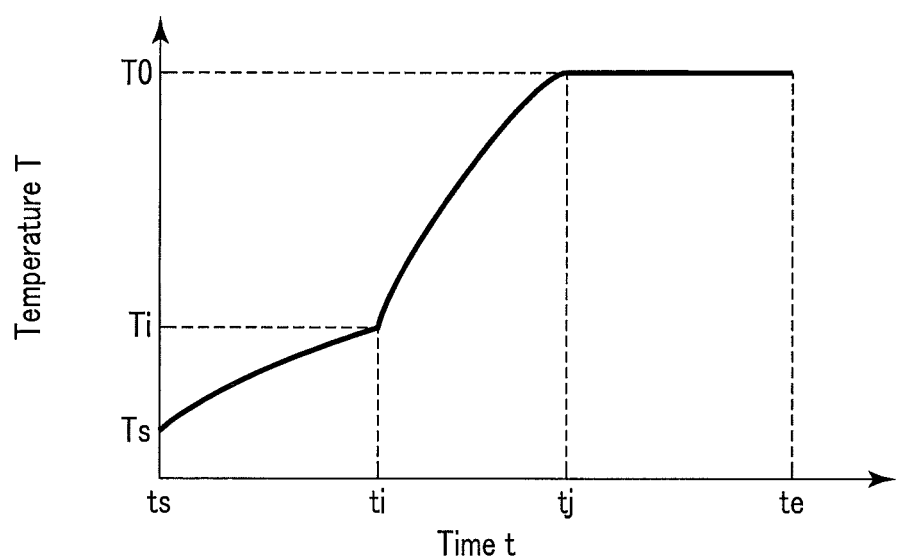
F I G. 17

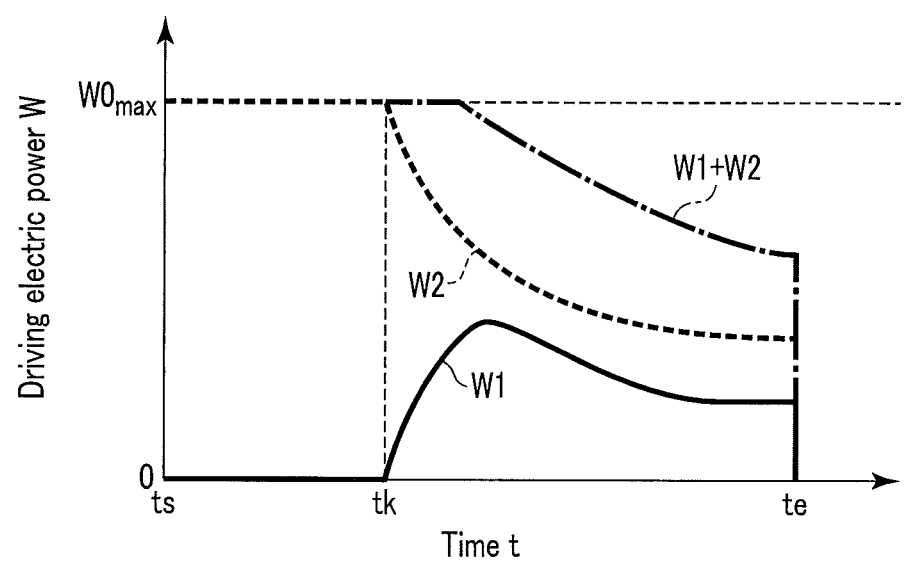
F I G. 19

ENERGY TREATMENT APPARATUS

CROSS-REFERENCE TO RELATED APPLICATIONS

This is a Continuation Application of PCT Application No. PCT/JP2015/077319, filed Sep. 28, 2015 and based upon and claiming the benefit of priority from prior Japanese Patent Application No. 2014-223527, filed Oct. 31, 2014, the entire contents of which are incorporated herein by reference.

BACKGROUND OF THE INVENTION

1. Field of the Invention

The present invention relates to an energy treatment apparatus which treats a treated target by use of energy supplied to a treatment portion.

2. Description of the Related Art

Jpn. Pat. Appln. KOKAI Publication No. 2012-96045 discloses an ultrasonic treatment instrument (energy treatment instrument) in which an ultrasonic vibration generated in an ultrasonic transducer including piezoelectric elements and others is transmitted to a treatment portion through a waveguide tube and which treats a treated target by use of the ultrasonic vibration that is energy supplied to the treatment portion. In this ultrasonic treatment instrument, a battery which is an electric power source is attached to a holding unit held by a surgeon. An energy generator which is driven due to source electric power (battery electric power) from the battery is provided in the ultrasonic treatment instrument. This energy generator is formed from a driving circuit, an amplifier circuit, and others, and is driven so as to generate vibration generating electric power as energy. The vibration generating electric power is supplied to the ultrasonic transducer, and the ultrasonic vibration is thereby generated in the ultrasonic transducer.

BRIEF SUMMARY OF THE INVENTION

According to one aspect of the invention, an energy treatment apparatus includes that: an electric power source in which maximum source electric power that is a maximum value of source electric power output per unit time is defined; a first energy generator to which first driving electric power is supplied due to the source electric power, and which is driven by the first driving electric power to generate first energy; a second energy generator to which second driving electric power is supplied due to the source electric power, and which is driven by the second driving electric power to generate second energy different from the first energy; a treatment portion configured to conduct a treatment by simultaneously using the first energy and the second energy; an electric power detector configured to detect the first driving electric power and the second driving electric power with time; and a controller which is configured to control the first energy generator and the second energy generator on the basis of a detection result in the electric power detector to keep the sum of the first driving electric power and the second driving electric power that are supplied per unit time less than or equal to the maximum source electric power of the electric power source continuously with time.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view schematically showing the exterior of an energy treatment instrument according to a first embodiment;

FIG. 4 is a schematic diagram showing the relation between impedance for a high-frequency electric current and first driving electric power in a state where a controller controls in a first energy mode according to the first embodiment;

FIG. 5 is a schematic diagram showing changes of the first driving electric power and second driving electric power with time in a state where the controller controls in the first energy mode according to the first embodiment;

FIG. 13 is a schematic diagram showing changes of the first driving electric power and the second driving electric power with time in a state where the energy or the energies is/are supplied to the treatment portion according to a first modification of the second embodiment;

FIG. 14 is a flowchart showing processing in the energy treatment instrument in a state where the energy or the energies for use in the treatment is/are supplied to the treatment portion according to a second modification of the second embodiment;

FIG. 15 is a schematic diagram showing changes of the first driving electric power and the second driving electric power with time in a state where the energy or the energies is/are supplied to the treatment portion according to the second modification of the second embodiment;

FIG. 16 is a schematic diagram showing a change of impedance for a high-frequency electric current with time in a state where the energy or the energies is/are supplied to the treatment portion according to the second modification of the second embodiment;

FIG. 17 is a schematic diagram showing a change of the temperature of a heating element with time in a state where the energy or the energies is/are supplied to the treatment portion according to the second modification of the second embodiment;

FIG. 19 is a schematic diagram showing changes of the first driving electric power and the second driving electric power with time in a state where the energy or the energies is/are supplied to the treatment portion according to the third modification of the second embodiment;

DETAILED DESCRIPTION OF THE INVENTION

First Embodiment

A first embodiment of the present invention is described with reference to FIG. 1 to FIG. 6.

Figure 2:
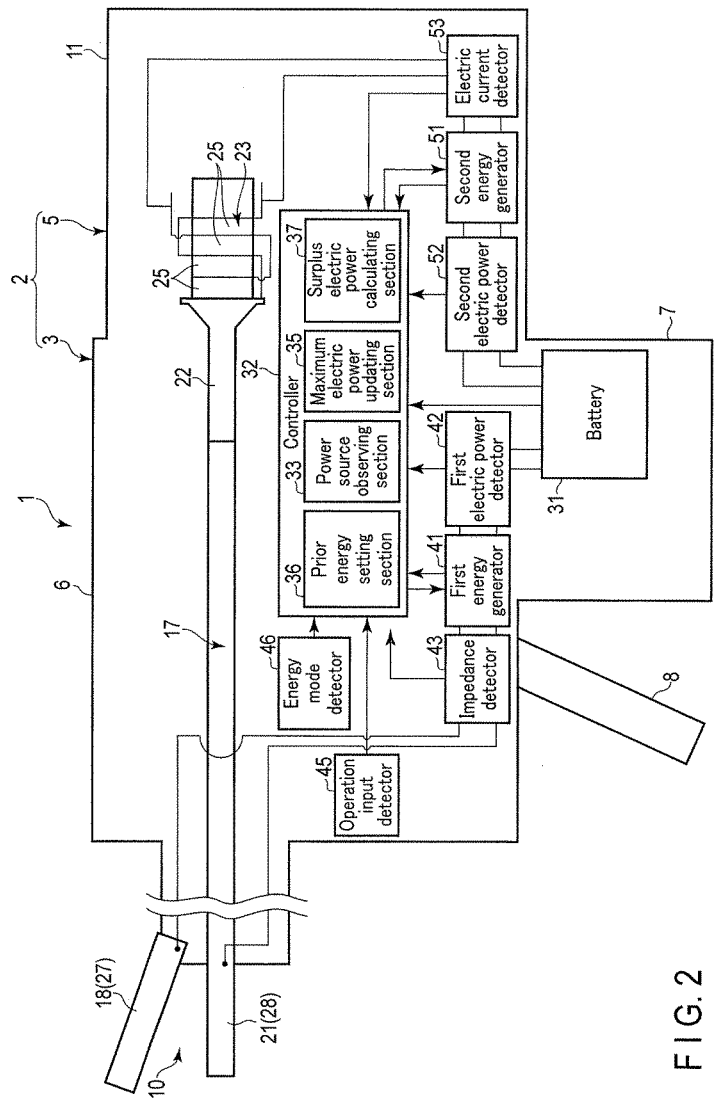
FIG. 2 is a schematic diagram showing the configuration of the energy treatment instrument according to the first embodiment.

FIG. 1 is a diagram showing the exterior of an energy treatment instrument (energy treatment apparatus) 1 according to the present embodiment. FIG. 2 is a diagram showing the configuration of the energy treatment instrument 1 including the inside thereof. As shown in FIG. 1, the energy treatment instrument 1 has a longitudinal axis C. One side in a longitudinal direction parallel to the longitudinal axis C is a distal side (an arrow C1 side in FIG. 1), and the side opposite to the distal side is a proximal side (an arrow C2 side in FIG. 1). In the present embodiment, the energy treatment instrument 1 treats a treated target such as a living tissue by simultaneously using high-frequency electric power P1 which is a first energy and an ultrasonic vibration (vibration generating electric power P2) which is a second energy different from the first energy.

As shown in FIG. 1 and FIG. 2, the energy treatment instrument 1 includes a holding unit 2 which can be held by a surgeon. The holding unit 2 includes a handle assembly 3 and a transducer assembly 5. The handle assembly 3 includes a case body portion (handle body portion) 6 extending along the longitudinal axis C, a fixed handle 7 extending from the case body portion 6 toward a direction that intersects with the longitudinal axis C, and a movable handle 8 which is attached to the case body portion 6 in a state to be openable and closable relative to the fixed handle 7. The transducer assembly 5 includes a transducer case 11 forming the exterior. When the transducer case 11 is coupled to the case body portion 6 from the proximal side, the transducer assembly 5 is coupled to the handle assembly 3, and the holding unit 2 is formed. In the holding unit 2, the transducer assembly 5 may be detachable from the handle assembly 3, or the transducer assembly 5 may not be detachable from the handle assembly 3.

The handle assembly 3 includes a rotational operation knob 12 which is a rotational operation input portion that is coupled to the case body portion 6 from the distal side. The rotational operation knob 12 is rotatable relative to the case body portion 6 around the longitudinal axis C. An energy operation button 13, which is an energy operation input portion, and a mode switch lever 15, that is a mode switch portion to which a switch operation of energy modes is input, are also attached to the case body portion 6.

The energy treatment instrument 1 includes a sheath 16 extending along the longitudinal axis C, a probe 17 which is inserted through the sheath 16, and a jaw 18 which is attached to the distal portion of the sheath 16. The sheath 16 is coupled to the handle assembly 3 from the distal side. Inside the case body portion 6 (inside the handle assembly 3), the sheath 16 is coupled to the transducer case 11. The probe 17 extends toward the distal side through the inside of the sheath 16 from the inside of the case body portion 6. The central axis of the probe 17 is the longitudinal axis C. A probe distal portion 21 protruding toward the distal side from the distal end of the sheath 16 is provided in the probe 17. The jaw 18 is rotatable relative to the sheath 16. When the movable handle 8 is opened or closed relative to the fixed handle 7, the jaw 18 turns, and the jaw 18 moves to open or close relative to the probe distal portion 21. The sheath 16, the probe 17, and the jaw 18 are rotatable around the longitudinal axis C relative to the case body portion 6 integrally with the rotational operation knob 12. A treatment portion (end effector) 10 which treats a treated target such as a living tissue by use of energies (the high-frequency electric power P1 and the ultrasonic vibration in the present embodiment) is formed by the probe distal portion 21 of the probe 17 and by the jaw 18. In the present embodiment, the treated target is grasped between the jaw 18 and the probe distal portion (probe treatment portion) 21 to conduct the treatment.

Inside the case body portion 6 (inside the handle assembly 3), a horn member 22 is connected to the proximal side of the probe 17. The horn member 22 is attached to (supported by) the transducer case 11. An ultrasonic transducer 23 which is a vibration generator is attached to the horn member 22. The ultrasonic transducer 23 is provided inside the transducer case 11 (inside the holding unit 2), and includes piezoelectric elements 25 (four piezoelectric elements 25 in the present embodiment). In the treatment portion 10, a jaw side electrode portion (electrode portion) 27 made of an electrically conductive material is provided in the jaw 18, and a probe side electrode portion (electrode portion) 28 made of an electrically conductive material is provided in the probe distal portion 21.

As shown in FIG. 2, a battery 31 which is an electric power source is provided inside the holding unit 2. The battery 31 outputs source electric power (battery electric power) W0 which is direct-current electric power. In the present embodiment, the battery 31 is removably attached to the holding unit 2. The battery 31 attached to the holding unit 2 may be disposed inside the fixed handle 7, or may be disposed inside the oscillator case 11. In the battery 31, maximum source electric power W0max which is the maximum value of the source electric power W0 output per unit time is defined at the time of manufacture. Therefore, the battery 31 does not output the source electric power W0 at an electric power value higher than the maximum source electric power W0max per unit time.

A controller 32 is also provided inside the holding unit 2. The controller 32 is formed from a central processing unit (CPU) or an application specific integrated circuit (ASIC), and a storage section such as a memory. The controller 32 includes a power source observing section 33, a maximum electric power updating section 35, a prior energy setting section 36, and a surplus electric power calculating section 37. The power source observing section 33, the maximum electric power updating section 35, the prior energy setting section 36, and the surplus electric power calculating section 37 are formed from, for example, electronic circuits provided in the CPU or ASIC. The battery 31 is observed with time by the power source observing section 33, and information regarding an observation result is acquired by the controller 32. A characteristic change of the battery 31 resulting from deterioration with time, a temperature change, and others is suitably detected by the observation of the battery 31. Accordingly, a change of the maximum source electric power W0max resulting from the characteristic change of the battery 31 is also suitably detected. The maximum source electric power W0max defined, for example, at the time of manufacture is stored in, for example, the storage section. When the change of the maximum source electric power W0max is detected, the defined maximum source electric power W0max stored in, for example, the storage section is updated by the maximum electric power updating section 35, and the updated maximum source electric power W0max is stored.

A first energy generator 41 and a second energy generator 51 are provided inside the holding unit 2. Each of the first energy generator 41 and the second energy generator 51 is electrically connected to the battery 31 via an interface such as a bus, and is formed from, for example, a driving circuit including an amplifier circuit. The driving state of the first energy generator 41 and the driving state of the second energy generator 51 are controlled by the controller 32, and the driving state of the first energy generator 41 and the driving state of the second energy generator 51 are fed back to the controller 32.

First driving electric power W1 is supplied to the first energy generator 41 due to the source electric power W0 output from the battery 31. The first energy generator 41 is driven by the first driving electric power W1, and the high-frequency electric power P1 is generated as first energy. The electric power value (degree) of the first driving electric power W1 changes in response to the driving state of the first energy generator 41. A first electric power detector (electric power detector) 42 which detects, with time, the first driving electric power W1 supplied to the first energy generator 41 is provided inside the holding unit 2. The first electric power detector 42 is formed from, for example, a detecting circuit, and a detection result in the first electric power detector 42 is transmitted to the controller 32 via an interface such as a bus.

The high-frequency electric power P1 generated in the first energy generator 41 is supplied to the jaw side electrode portion 27 and the probe side electrode portion 28 that are provided in the treatment portion 10. The jaw side electrode portion 27 and the probe side electrode portion 28 are supplied with the high-frequency electric power P1 and thereby function as electrodes of the high-frequency electric power P1, and a high-frequency voltage (potential difference) V1 is generated between the jaw side electrode portion 27 and the probe side electrode portion 28. In this state, the treated target is grasped between the jaw 18 and the probe distal portion 21, and a high-frequency electric current I1 flows through the treated target between the jaw side electrode portion 27 and the probe side electrode portion 28 (i.e. between the electrode portions 27 and 28). The treatment portion 10 conducts a treatment by use of the high-frequency electric power P1 supplied as the first energy as described above. An impedance detector 43 which detects, with time, impedance Z1 (i.e. impedance of the treated target) for the high-frequency electric current I1 is provided inside the holding unit 2. The impedance detector 43 is formed from, for example, a detecting circuit, and a detection result of the impedance (high-frequency impedance) Z1 is transmitted to the controller 32 via an interface such as a bus. The electric power value of the high-frequency electric power P1 which is the first energy changes in response to the electric power value of the first driving electric power W1, and when the first driving electric power W1 is constant with time, the high-frequency electric power P1 is also constant with time. As the first driving electric power W1 increases, the high-frequency electric power P1 also increases.

Second driving electric power W2 is supplied to the second energy generator 51 due to the source electric power W0 output from the battery 31. The second energy generator 51 is driven by the second driving electric power W2, and the vibration generating electric power P2 is generated as second energy different from the first energy. The electric power value (degree) of the second driving electric power W2 changes in response to the driving state of the second energy generator 51. A second electric power detector (electric power detector) 52 which detects, with time, the second driving electric power W2 supplied to the second energy generator 51 is provided inside the holding unit 2. The second electric power detector 52 is formed from, for example, a detecting circuit, and a detection result in the second electric power detector 52 is transmitted to the controller 32 via an interface such as a bus.

The vibration generating electric power P2 generated in the second energy generator 51 is supplied to the ultrasonic transducer (vibration generator) 23 provided inside the transducer case 11. When the vibration generating electric power P2 is supplied to the ultrasonic oscillator 23, a vibration generating electric current I2 which is an alternating electric current flows through each of the piezoelectric elements 25, and the vibration generating electric current I2 is converted into an ultrasonic vibration in each of the piezoelectric elements 25. As a result, the ultrasonic vibration is generated in the ultrasonic transducer 23. The generated ultrasonic vibration is transmitted to the probe distal portion 21 toward the distal side through the horn member 22 and the probe 17. The treatment portion 10 then conducts a treatment by use of the ultrasonic vibration supplied as the second energy. An electric current detector 53 which detects, with time, the vibration generating electric current I2 is provided inside the holding unit 2. The electric current detector 53 is formed from, for example, a detecting circuit, and a detection result of the vibration generating electric current I2 (e.g. an effective value of the alternating electric current) is transmitted to the controller 32 via an interface such as a bus. The electric power value of the vibration generating electric power P2 which is the second energy changes in response to the electric power value of the second driving electric power W2, and when the second driving electric power W2 is constant with time, the vibration generating electric power P2 is also constant with time. As the second driving electric power W2 increases, the vibration generating electric power P2 also increases.

An operation input detector 45 which detects the input of an energy operation in the energy operation button 13 is provided inside the holding unit 2 (inside the case body portion 6). The operation input detector 45 is, for example, a switch which changes its on/off state in response to whether or not there is an input of the energy operation. When the operation input detector 45 detects the input of the energy operation, an operation signal indicating the input of the energy operation is transmitted to the controller 32 through, for example, a signal path. When the operation signal is transmitted, the controller 32 controls the first energy generator 41 and the second energy generator 51 so that the first driving electric power W1 is supplied to the first energy generator 41 and so that the second driving electric power W2 is supplied to the second energy generator 51. As a result, the high-frequency electric power (first energy) P1 is generated in the first energy generator 41, and the vibration generating electric power (second energy) P2 is generated in the second energy generator 51 at the same time. Then the high-frequency electric power (first energy) P1 and the ultrasonic vibration (second energy) are supplied to the treatment portion 10 at the same time.

An energy mode detector 46 which detects energy modes that are switched on the basis of the switch operation of the mode switch lever 15 is provided inside the holding unit 2. The energy mode detector 46 is, for example, a sensor which detects the position of the mode switch lever 15, and a detection result in the energy mode detector 46 is transmitted to the controller 32 via an interface such as a bus. The energy modes are switched between a first energy mode and a second energy mode. The prior energy setting section 36 of the controller 32 sets one of the first energy (the high-frequency electric power P1) and the second energy (the vibration generating electric power P2 and the ultrasonic vibration) that is higher in priority in the treatment with the treatment portion 10 on the basis of the detection result in the energy mode detector 46. In the present embodiment, the high-frequency electric power P1 is set as prior energy higher in priority in the first energy mode, and the vibration generating electric power P2 and the ultrasonic vibration are set as prior energies higher in priority in the second energy mode.

The driving electric power (W1 or W2) to be supplied to the energy generator (41 or 51) which generates the prior energy is prior driving electric power. In the first energy mode, the first driving electric power W1 to be supplied to the first energy generator 41 which generates the high-frequency electric power P1 that is the prior energy is the prior driving electric power. In the second energy mode, the second driving electric power W2 to be supplied to the second energy generator 51 which generates the vibration generating electric power P2 that is the prior energy is the prior driving electric power. The surplus electric power calculating section 37 of the controller 32 calculates, with time, surplus electric power (Q1 or Q2) that is a difference value in which the prior driving electric power (W1 or W2) is subtracted from the maximum source electric power W0max of the battery 31, in a state where the supply of the first driving electric power W1 to the first energy generator 41 and the supply of the second driving electric power W2 to the second energy generator 51 are performed at the same time. In the first energy mode, the first surplus electric power Q1 in which the first driving electric power W1 that is the prior driving electric power is subtracted from the maximum source electric power W0max of the battery 31 is calculated with time. In the second energy mode, the second surplus electric power Q2 in which the second driving electric power W2 that is the prior driving electric power is subtracted from the maximum source electric power W0max of the battery 31 is calculated with time. On the basis of the surplus electric power (Q1 or Q2) that is calculated with time, the controller 32 controls the first energy generator 41 and the second energy generator 51.

Next, functions and advantageous effects of the energy treatment instrument 1 are described. When a treated target such as a living tissue is treated by use of the energy treatment instrument 1, the surgeon holds the holding unit 2 to insert the sheath 16, the probe 17, and the jaw 18 into a body. The treated target is then disposed between the probe distal portion 21 and the jaw 18, and the movable handle 8 is closed relative to the fixed handle 7. As a result, the jaw 18 is closed relative to the probe distal portion 21, and the treated target is grasped between the jaw 18 and the probe distal portion 21. In a state where the treated target is grasped, an energy operation is input with the energy operation button 13.

Figure 3:
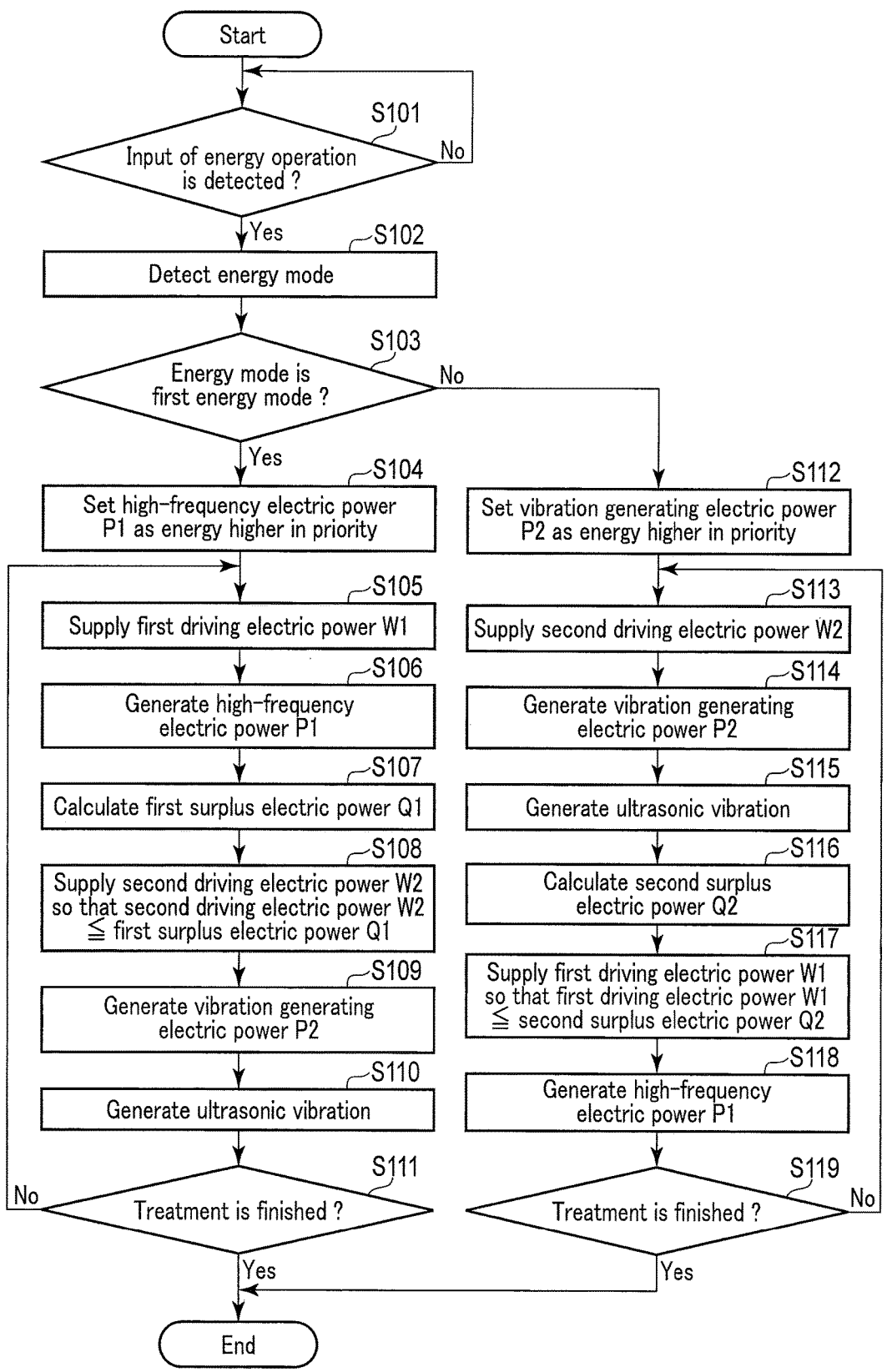
FIG. 3 is a flowchart showing processing in the energy treatment instrument in a state where energies for use in a treatment are supplied to a treatment portion according to the first embodiment.

FIG. 3 is a flowchart showing processing in the energy treatment instrument 1 in a state where energies (the first energy and the second energy) for use in a treatment are supplied to the treatment portion 10. As shown in FIG. 3, when an energy operation is input, the operation input detector 45 detects the input of the energy operation (step S101—Yes). When the input of the energy operation is detected, the energy mode detector 46 detects an energy mode (step S102). When the detected energy mode is the first energy mode (step S103—Yes), the prior energy setting section 36 sets the high-frequency electric power P1 which is the first energy as energy higher in priority in the treatment with the treatment portion 10 (step S104). Thus, the first driving electric power W1 that is supplied to the first energy generator 41 is prior driving electric power.

When the high-frequency electric power P1 is set as the prior energy, the controller 32 controls the driving state of the first energy generator 41 to supply the first driving electric power W1 to the first energy generator 41 (step S105). In this instance, the first driving electric power W1 is lower than the maximum source electric power W0max of the battery 31. The first energy generator 41 generates the high-frequency electric power P1 as the first energy by the supply of the first driving electric power W1 (step S106). The high-frequency electric power P1 is then supplied to the jaw side electrode portion 27 and the probe side electrode portion 28 of the treatment portion 10, and the high-frequency voltage (potential difference) V1 is generated between the jaw side electrode portion 27 and the probe side electrode portion 28. Accordingly, the high-frequency electric current I1 flows through the treated target between the jaw side electrode portion 27 and the probe side electrode portion 28. In this instance, the impedance detector 43 detects the impedance (high-frequency impedance) Z1 of the treated target with time. By the flow of the high-frequency electric current I1 through the treated target, the treated target is degenerated and coagulated.

In the first energy mode in which the first driving electric power W1 is the prior driving electric power, the controller 32 controls the first energy generator 41 on the basis of the impedance Z1, and adjusts the electric power value of the first driving electric power W1. By the adjustment of the first driving electric power W1, the high-frequency electric power P1 which changes in response to the first driving electric power W1 is adjusted. The high-frequency electric power P1 is as shown in Equation (1) by use of the high-frequency electric current I1, the high-frequency voltage V1, and the impedance Z1.

[Equation 1]

$$P1 = I1 \cdot V1 = I1^2 \cdot Z1 = V1^2/Z1 \tag{1}$$

FIG. 4 is a diagram showing the relation (i.e. load characteristics of the first driving electric power W1) between the impedance Z1 for the high-frequency electric current I1 and the first driving electric power W1 in a state where the controller 32 controls in the first energy mode. In FIG. 4, the impedance Z1 is indicated on the abscissa axis, and the first driving electric power W1 is indicated on the ordinate axis. Because the high-frequency electric power P1 changes in response to the first driving electric power W1, load characteristics (change characteristics) similar to those in FIG. 4 are also shown for the impedance Z1 when the high-frequency electric power P1 is indicated on the ordinate axis instead of the first driving electric power W1. In the first energy mode, the controller 32 changes the first driving electric power W1 relative to the impedance Z1 as shown in FIG. 4 on the basis of the detection result of the impedance Z1. Here, control of the first driving electric power W1 to keep the high-frequency electric current I1 that is an electric current, which flows through the treated target by the supply of the first driving electric power W1, constant with time is constant current control, and control of the first driving electric power W1 to keep the first driving electric power W1 (the high-frequency electric power P1) constant with time is constant electric power control. Moreover, control of the first driving electric power W1 to keep the high-frequency voltage V1, which is a voltage to be applied across the jaw side electrode portion 27 and the probe side electrode portion 28 by the supply of the first driving electric power W1, constant with time is constant voltage control.

On the basis of the detection result of the impedance Z1, the controller 32 adjusts the first driving electric power W1 by one of the constant current control, the constant electric power control, and the constant voltage control so that the first driving electric power W1 may be lower. For example, when the impedance Z1 is a value close to 0 (when the impedance Z1 is Z1p or less in FIG. 4), the constant current control is performed. When the impedance Z1 is high (when the impedance Z1 is more than Z1q in FIG. 4), the constant voltage control is performed. When the impedance Z1 is higher than a range in which the constant current control is performed and is lower than a range in which the constant voltage control is performed (when the impedance Z1 is more than Z1p and is less than or equal to Z1q in FIG. 4), the constant electric power control (at an electric power value W1p in FIG. 4) is performed.

As shown in FIG. 3, when the high-frequency electric power P1 is generated by the first driving electric power W1 (step S106), the surplus electric power calculating section 37 calculates, with time, the first surplus electric power Q1 in which the first driving electric power W1 that is the prior driving electric power is subtracted from the maximum source electric power W0max of the battery 31 (step S107). The controller 32 then controls the driving state of the second energy generator 51 on the basis of the calculated first surplus electric power Q1, and supplies the second driving electric power W2 to the second energy generator 51 (step S108). By the supply of the second driving electric power W2, the second energy generator 51 generates the vibration generating electric power P2 as the second energy (step S109). The vibration generating electric power P2 is then supplied to the ultrasonic transducer 23, and the ultrasonic transducer 23 generates an ultrasonic vibration (step S110). When the ultrasonic vibration is transmitted to the probe distal portion 21 of the treatment portion 10 as the second energy, the probe distal portion 21 vibrates, and frictional heat is generated between the probe distal portion 21 and the grasped treated target. The treated target is coagulated and cut at the same time by the frictional heat. In general, coagulation performance by the ultrasonic vibration is lower than coagulation performance by the high-frequency electric current. In a state where the vibration generating electric power P2 is supplied to the ultrasonic transducer 23, a vibration generating voltage (electric potential difference) V2 is applied to the piezoelectric elements 25. The vibration generating electric current I2 then flows through each of the piezoelectric elements 25. In this instance, the electric current detector 53 detects the vibration generating electric current I2 with time.

In step S108, the second driving electric power W2 is supplied to the second energy generator 51 in a state where the second driving electric power W2 is less than or equal to the calculated first surplus electric power Q1. That is, the controller 32 controls the second driving electric power W2 in a range in which the second driving electric power W2 is less than or equal to the first surplus electric power Q1. Therefore, Equation (2) is satisfied in the first energy mode in which the first driving electric power W1 is the prior driving electric power.

[Equation 2]

$$W2 \leq Q1 = W0\max - W1 \tag{2}$$

When Equation (2) is satisfied, Equation (3) is satisfied.

[Equation 3]

$$W1 + W2 \leq W0\max \tag{3}$$

Therefore, in the first energy mode, the sum (W1+W2) of the first driving electric power W1 and the second driving electric power W2 that are supplied per unit time is less than or equal to the maximum source electric power W0max of the battery (electric power source) 31. When the treatment in the first energy mode is continued (step S111—No), steps S105 to S110 are repeated with time.

FIG. 5 is a diagram showing changes of the first driving electric power W1 and the second driving electric power W2 with time in a state where the controller 32 controls in the first energy mode. In FIG. 5, a time t is indicated on the abscissa axis, the supply start time of the first driving electric power W1 and the second driving electric power W2 is indicated by ts, and the supply stop time of the first driving electric power W1 and the second driving electric power W2 is indicated by te. The time from ts to te is about 2 to 5 seconds. Moreover, in FIG. 5, the driving electric powers (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

In a treatment using the high-frequency electric power P1, the treated target is degenerated and the temperature of the treated target rises due to the flow of the high-frequency electric current I1 through the treated target. As a result of the degeneration and temperature rise of the treated target, the impedance (high-frequency impedance) Z1 for the high-frequency electric current I1 increases. Thus, when a certain period of time passes since the supply start time ts of the first driving electric power W1 and the second driving electric power W2, the impedance Z1 increases to a range in which the constant voltage control to keep the high-frequency voltage V1 constant with time is performed. Therefore, when a certain period of time passes since the supply start time ts, a switch is made from the constant electric power control to keep the first driving electric power (the high-frequency electric power P1) constant with time to the aforementioned constant voltage control. Due to the switch of the control of the first driving electric power W1 to the constant voltage control, the first driving electric power W1 decreases with time as shown in FIG. 5.

In the first energy mode, the first driving electric power W1 to generate the high-frequency electric power P1 which is the prior energy is supplied by priority. Thus, in the first energy mode, the high-frequency electric power P1 is generated by priority over the vibration generating electric power P2. Therefore, in the first energy mode, a treatment higher in coagulation performance than in cutting performance is conducted by the treatment portion 10.

In the first energy mode, the second driving electric power W2 is supplied to the second energy generator 51 in a range less than or equal to the first surplus electric power Q1 in which the first driving electric power W1 is subtracted from the maximum source electric power W0max of the battery 31. That is, in the first energy mode, the controller 32 keeps the second driving electric power W2 less than or equal to the first surplus electric power Q1 continuously with time. Because the second driving electric power W2 is kept less than or equal to the first surplus electric power Q1 continuously with time, the sum of the first driving electric power W1 and the second driving electric power W2 that are supplied per unit time is kept less than or equal to the maximum source electric power W0max of the battery 31 continuously with time in the first energy mode. In the first energy mode according to the present embodiment, the second driving electric power W2 increases with time in a range less than or equal to the first surplus electric power Q1 in response to the decrease of the first driving electric power W1 with time after the control of the first driving electric power W1 is switched to the constant voltage control.

Here, the maximum value of the first driving electric power W1 that is supplied per unit time in a state where the first driving electric power W1 is supplied to the first energy generator 41 is first maximum driving electric power W1max. The first maximum driving electric power W1max is less than or equal to the maximum source electric power W0max of the battery 31. For example, in the first energy mode, the first driving electric power W1 is supplied at the first maximum driving electric power W1max which is the maximum value at a time ta. However, at the time ta, an electric power value W2a of the second driving electric power W2 is less than or equal to an electric power value Q1a of the first surplus electric power Q1. Thus, even at the time ta when the first driving electric power W1 is the first maximum driving electric power W1max which is the maximum value, the sum of the first driving electric power W1 and the second driving electric power W2 is less than or equal to the maximum source electric power W0max of the battery 31.

As shown in FIG. 3, when the energy mode detected by the energy mode detector 46 is the second energy mode (step S103—No), the prior energy setting section 36 sets the vibration generating electric power P2 and the ultrasonic vibration which are the second energies as energies higher in priority in the treatment with the treatment portion 10 (step S212). Thus, the second driving electric power W2 that is supplied to the second energy generator 51 is prior driving electric power.

When the vibration generating electric power P2 (ultrasonic vibration) is set as the prior energy, the controller 32 controls the driving state of the second energy generator 51, and supplies the second driving electric power W2 to the second energy generator 51 (step S113). In this instance, the second driving electric power W2 is lower than the maximum source electric power W0max of the battery 31. The second energy generator 51 generates the vibration generating electric power P2 as the second energy by the supply of the second driving electric power W2 (step S114). The vibration generating electric power P2 is then supplied to the ultrasonic transducer 23, and the ultrasonic transducer 23 generates the ultrasonic vibration (step S115). When the ultrasonic vibration is transmitted to the probe distal portion 21 of the treatment portion 10 as the second energy, the treated target is coagulated and cut at the same time by the frictional heat as has been described above in connection with the first energy mode.

The amplitude of the ultrasonic vibration generated in the ultrasonic transducer 23 is proportional to the electric current value (effective value) of the vibration generating electric current (alternating electric current) I2. In the second energy mode in which the ultrasonic vibration is the prior energy, it is desired that the amplitude of the ultrasonic vibration in the probe distal portion 21 be kept constant with time from the viewpoint of treatment performance. In the present embodiment, the controller 32 controls the second energy generator 51 on the basis of the detected vibration generating electric current I2. In this way, the electric power value of the second driving electric power W2 is adjusted so that the vibration generating electric current I2 will be constant with time, and the vibration generating electric power P2 which changes in response to the second driving electric power W2 is adjusted. That is, to control the second driving electric power W2, the constant current control to keep the vibration generating electric current I2 constant with time is performed. The vibration generating electric current I2 is as shown in Equation (4) by use of impedance (acoustic impedance) Z2 for the vibration generating electric current I2, the vibration generating electric power P2, and the vibration generating voltage V2.

[Equation 4]

$$I2 = V2/Z2 = P2/V2 \qquad (4)$$

Thus, in the constant current control to keep the vibration generating electric current I2 constant with time, the vibration generating electric power P2 and the vibration generating voltage V2 need to be increased as the impedance Z2 increases. Therefore, the second driving electric power W2 which changes in response to the vibration generating electric power P2 needs to be increased as the impedance Z2 increases.

When the ultrasonic vibration is generated by the second driving electric power W2 (step S115), the surplus electric power calculating section 37 calculates, with time, the second surplus electric power Q2 in which the second driving electric power W2 that is the prior driving electric power is subtracted from the maximum source electric power W0max of the battery 31 (step S116). The controller 32 then controls the driving state of the first energy generator 41 on the basis of the calculated second surplus electric power Q2, and supplies the first driving electric power W1 to the first energy generator 41 (step S117). By the supply of the first driving electric power W1, the first energy generator 41 generates the high-frequency electric power P1 as the first energy (step S118). The high-frequency electric power P1 is then supplied to the jaw side electrode portion 27 and the probe side electrode portion 28 of the treatment portion 10, and the treated target is degenerated and coagulated as has been described above in connection with the first energy mode.

In step S117, the first driving electric power W1 is supplied to the first energy generator 41 in a state where the first driving electric power W1 is less than or equal to the calculated second surplus electric power Q2. That is, the controller 32 controls the first driving electric power W1 in a range in which the first driving electric power W1 is less than or equal to the second surplus electric power Q2. Therefore, Equation (5) is satisfied in the second energy mode in which the second driving electric power W2 is the prior driving electric power.

[Equation 5]

$$W1 \le Q2 = W0\text{max} - W2 \tag{5}$$

When Equation (5) is satisfied, Equation (3) is satisfied in the second energy mode as well as in the first energy mode. Therefore, in the second energy mode as well, the sum (W1+W2) of the first driving electric power W1 and the second driving electric power W2 that are supplied per unit time is less than or equal to the maximum source electric power W0max of the battery (electric power source) 31. When the treatment in the second energy mode is continued (step S119—No), steps S113 to S118 are repeated with time.

Figure 6:
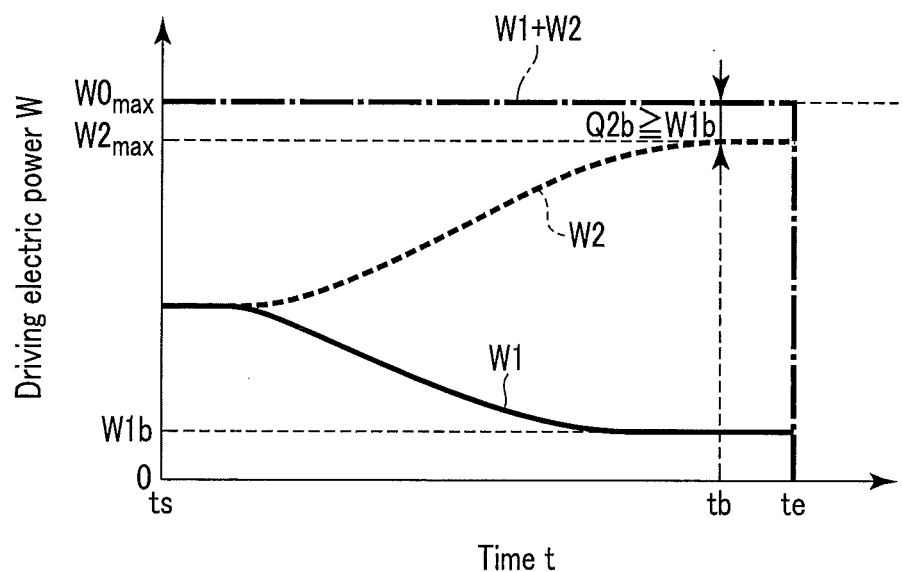
FIG. 6 is a schematic diagram showing changes of the first driving electric power and the second driving electric power with time in a state where the controller controls in a second energy mode according to the first embodiment.

FIG. 6 is a diagram showing changes of the first driving electric power W1 and the second driving electric power W2 with time in a state where the controller 32 controls in the second energy mode. In FIG. 6, the time t is indicated on the abscissa axis, the supply start time of the first driving electric power W1 and the second driving electric power W2 is indicated by ts, and the supply stop time of the first driving electric power W1 and the second driving electric power W2 is indicated by te. Moreover, in FIG. 6, the driving electric powers (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

In a treatment using the ultrasonic vibration (vibration generating electric power P2), water in the treated target is evaporated due to the frictional heat generated by the ultrasonic vibration, and the treated target is hardened. As a result of the hardening of the treated target, a load on the ultrasonic vibration increases, and the impedance (acoustic impedance) Z2 for the vibration generating electric current I2 increases. In the control of the second driving electric power W2, the constant current control to keep the vibration generating electric current I2 constant with time is performed. Thus, when a certain period of time passes since the supply start time is of the first driving electric power W1 and the second driving electric power W2, the impedance Z2 increases, and the vibration generating electric power P2 (the vibration generating voltage V2) increases. Because the vibration generating electric power P2 increases, the second driving electric power W2 which changes in response to the vibration generating electric power P2 increases with time as shown in FIG. 5.

In the second energy mode, the second driving electric power W2 to generate the vibration generating electric power P2 which is the prior energy is supplied by priority. Thus, in the second energy mode, the vibration generating electric power P2 (ultrasonic vibration) is generated by priority over the high-frequency electric power P1. Therefore, in the second energy mode, a treatment higher in cutting performance than in coagulation performance is conducted by the treatment portion 10.

In the second energy mode, the first driving electric power W1 is supplied to the first energy generator 41 in a range less than or equal to the second surplus electric power Q2 in which the second driving electric power W2 is subtracted from the maximum source electric power W0max of the battery 31. That is, in the second energy mode, the controller 32 keeps the first driving electric power W1 less than or equal to the second surplus electric power Q2 continuously with time. Because the first driving electric power W1 is kept less than or equal to the second surplus electric power Q2 continuously with time, the sum of the first driving electric power W1 and the second driving electric power W2 that are supplied per unit time is kept less than or equal to the maximum source electric power W0max of the battery 31 continuously with time in the second energy mode. In the second energy mode according to the present embodiment, the first driving electric power W1 decreases with time in a range less than or equal to the second surplus electric power Q2 in response to the increase of the second driving electric power W2 with time.

Here, the maximum value of the second driving electric power W2 that is supplied per unit time in a state where the second driving electric power W2 is supplied to the second energy generator 51 is second maximum driving electric power W2max. The second maximum driving electric power W2max is less than or equal to the maximum source electric power W0max of the battery 31. For example, in the second energy mode, the second driving electric power W2 is supplied at the second maximum driving electric power W2max which is the maximum value at a time tb. However, at the time tb, an electric power value W1b of the first driving electric power W1 is less than or equal to an electric power value Q2b of the second surplus electric power Q2. Thus, even at the time tb when the second driving electric power W2 is the second maximum driving electric power W2max which is the maximum value, the sum of the first driving electric power W1 and the second driving electric power W2 is less than or equal to the maximum source electric power W0max of the battery 31.

In the present embodiment, the maximum source electric power W0max of the battery 31 is lower than the sum of the first maximum driving electric power W1max which is the maximum value of the first driving electric power W1 and the second maximum driving electric power W2max which is the maximum value of the second driving electric power W2. That is, Equation (6) is satisfied.

[Equation 6]

$$W1\text{max} + W2\text{max} \ge W0\text{max} \tag{6}$$

In the present embodiment, the first driving electric power W1 and the second driving electric power W2 are controlled as described above, so that even when the sum of the first maximum driving electric power W1max and the second maximum driving electric power W2max is higher than the maximum source electric power W0max of the battery 31, the sum of the first driving electric power W1 and the second driving electric power W2 that are supplied per unit time is kept less than or equal to the maximum source electric power W0max of the battery 31 continuously with time in both the first energy mode and the second energy mode. Because the control to always keep the sum of the first driving electric power W1 and the second driving electric power W2 less than or equal to the maximum source electric power W0max of the battery 31 is performed, the battery 31 which outputs low source electric power (electric capacity) W0 can be used in the energy treatment instrument 1. That is, the maximum source electric power W0max of the battery 31 which is the electric power source used in the energy treatment instrument 1 can be reduced. Therefore, it is possible to provide the energy treatment instrument 1 which suitably conducts a treatment by simultaneously using energies (the high-frequency electric power P1 and the ultrasonic vibration in the present embodiment) without the increase of the source electric power W0 output from the battery 31.

The battery 31 is reduced in size and weight by the reduction of the source electric power W0 (the maximum source electric power W0max) of the battery 31. Operability in a treatment by the surgeon who holds the holding unit 2 can be improved by the reduction of the battery 31 in size and weight.

In the present embodiment, one of the first energy and the second energy that is higher in priority in the treatment is set, and the prior driving electric power (W1 or W2) to generate the prior energy is supplied by priority. Thus, even when the sum of the first driving electric power W1 and the second driving electric power W2 is kept less than or equal to the maximum source electric power W0max, the prior energy higher in priority in the treatment is suitably generated in the energy generator (41 or 51). Therefore, even when the sum of the first driving electric power W1 and the second driving electric power W2 is kept less than or equal to the maximum source electric power W0max, the prior energy is suitably supplied to the treatment portion 10, and treatment performance can be ensured.

In the present embodiment, the battery 31 is observed by the power source observing section 33 with time, and the change of the maximum source electric power W0max resulting from a characteristic change of the battery 31 is suitably detected. When the change of the maximum source electric power W0max is detected, the defined maximum source electric power W0max is updated by the maximum electric power updating section 35. When the defined maximum source electric power W0max is updated, the controller 32 controls the first driving electric power W1 and the second driving electric power W2 as described above by use of the updated maximum source electric power W0max. That is, the controller 32 keeps the sum of the first driving electric power W1 and the second driving electric power W2 that are supplied per unit time less than or equal to the updated maximum source electric power W0max of the battery 31 continuously with time. Therefore, even when the maximum source electric power W0max of the battery 31 has changed, the first driving electric power W1 and the second driving electric power W2 can be suitably controlled by use of the changed maximum source electric power W0max.

Modification of the First Embodiment

Figure 7:
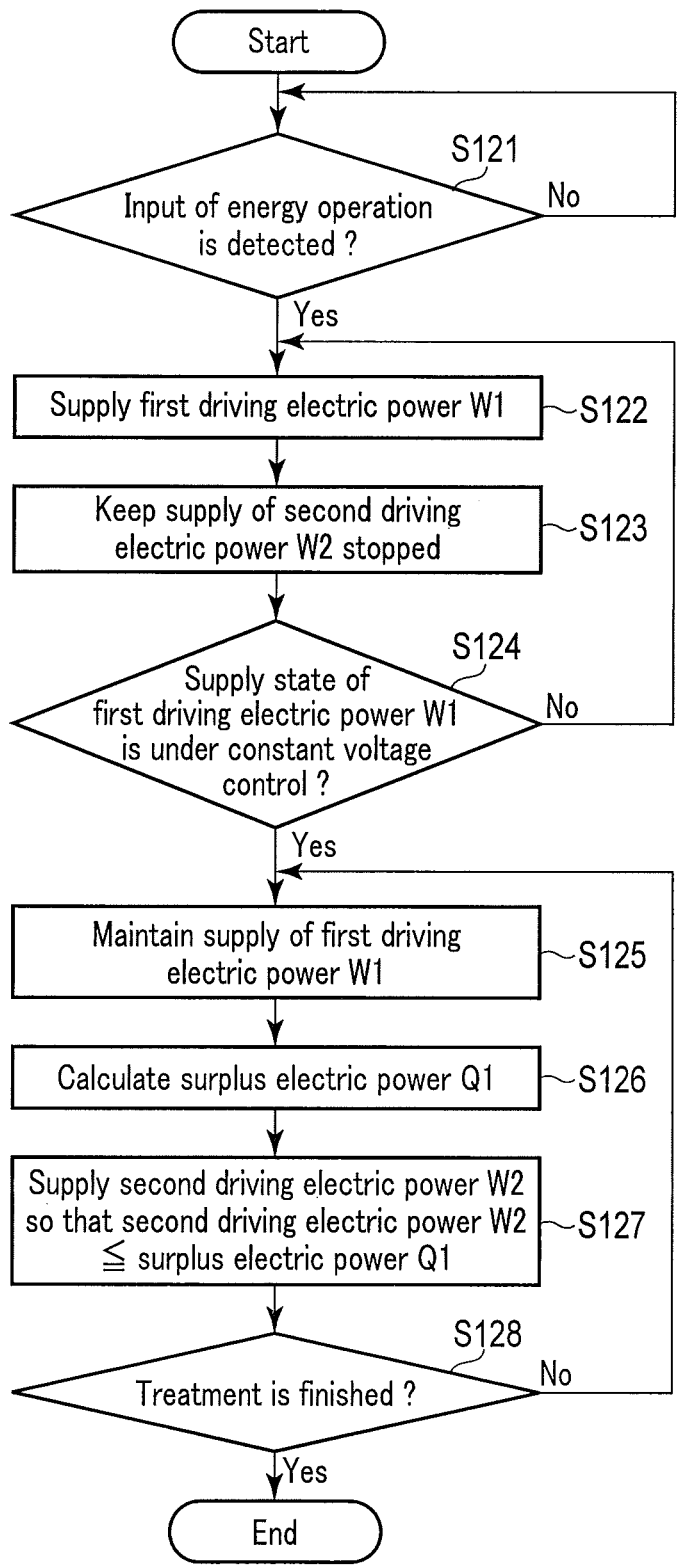
FIG. 7 is a flowchart showing processing in the energy treatment instrument in a state where the energy or the energies for use in the treatment is/are supplied to the treatment portion according to a first modification of the first embodiment.
Figure 8:
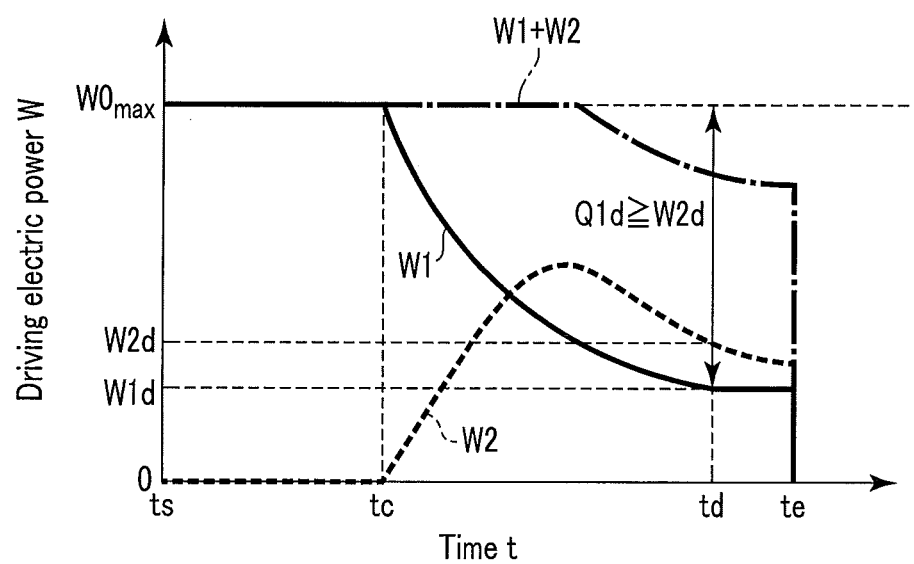
FIG. 8 is a schematic diagram showing changes of the first driving electric power and the second driving electric power with time in a state where the energy or the energies is/are supplied to the treatment portion according to the first modification of the first embodiment.

Next, a first modification of the first embodiment shown in FIG. 7 and FIG. 8 is described. In the present modification, the prior energy setting section 36 is not provided, and the prior energy higher in priority is not set, in contrast with the first embodiment. FIG. 7 is a flowchart showing processing in the energy treatment instrument 1 in a state where the energy or the energies for use in the treatment is/are supplied to the treatment portion 10. FIG. 8 is a diagram showing changes of the first driving electric power W1 and the second driving electric power W2 with time in a state where the energy or the energies is/are supplied to the treatment portion 10. In FIG. 8, the time t is indicated on the abscissa axis, and the driving electric powers (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

As shown in FIG. 7, in the present modification, when the operation input detector 45 detects the input of an energy operation (step S121—Yes), the controller 32 controls the driving state of the first energy generator 41 to supply the first driving electric power W1 to the first energy generator 41 (step S122). The first energy generator 41 generates the high-frequency electric power P1 as the first energy by the supply of the first driving electric power W1, and the treated target is coagulated by the high-frequency electric current I1 as in the first embodiment. In the present modification as well as in the first energy mode according to the first embodiment, the first driving electric power W1 is controlled so that the load characteristics (change characteristics) of the first driving electric power W1 for the impedance Z1 may be similar to the load characteristics shown in FIG. 4 on the basis of the detection result of the impedance (high-frequency impedance) Z1. Therefore, the controller 32 adjusts the first driving electric power W1 by one of the constant current control, the constant electric power control, and the constant voltage control on the basis of the detection result of the impedance Z1 so that the first driving electric power W1 may be lower.

Even if the supply of the first driving electric power W1 is started, the controller 32 controls the driving state of the second energy generator 51 to keep the supply of the second driving electric power W2 to the second energy generator 51 stopped (step S123). Therefore, at the start of the treatment with the treatment portion 10, the controller 32 starts the supply of the first driving electric power W1 to the first energy generator 41 without supplying the second driving electric power W2 to the second energy generator 51. In this instance, as shown in FIG. 8, the first driving electric power W1 is supplied in a state where the electric power value of the first driving electric power W1 is the same as the maximum source electric power W0max of the battery 31. However, the second driving electric power W2 is not supplied, so that as in the first embodiment, the sum of the first driving electric power W1 and the second driving electric power W2 that are supplied per unit time is kept less than or equal to the maximum source electric power W0max of the battery 31 (actually, the same as the maximum source electric power W0max) continuously with time, and Equation (3) above is satisfied. In FIG. 8, the supply start time of the first driving electric power W1 is indicated by ts, and the supply stop time of the first driving electric power W1 and the second driving electric power W2 is indicated by te.

The high-frequency electric current I1 flows through the treated target in a state where the second driving electric power W2 is not supplied and the first driving electric power W1 alone is supplied, so that when a certain period of time passes since the supply start time is of the first driving electric power W1, the impedance (high-frequency impedance) Z1 increases to a range in which the constant voltage control to keep the high-frequency voltage V1 constant with time is performed. That is, the supply state of the first driving electric power W1 is switched by the controller 32 from the constant electric power control to keep the first driving electric power W1 constant with time to the constant voltage control, in response to the change of the impedance Z1 with time. Due to the switch to the constant voltage control, the electric power value of the first driving electric power W1 starts to decrease (from the maximum source electric power W0max in the present modification). When a switch to the constant voltage control is not made (step S124—No), steps S122 and S123 are repeated with time until a switch to the constant voltage control is made (i.e. until the first driving electric power W1 starts to decrease). In FIG. 8, the supply state of the first driving electric power W1 is switched from the constant electric power control to the constant voltage control at a time tc. In the present modification, the electric power value (W1p in FIG. 4) of the first driving electric power W1 under the constant electric power control is the same as the maximum source electric power W0max of the battery 31.

When the supply state of the first driving electric power W1 is switched to the constant voltage control (step S124—Yes), the controller 32 maintains the supply of the first driving electric power W1 (step S125), and the surplus electric power calculating section 37 calculates, with time, the surplus electric power (first surplus electric power) Q1 in which the first driving electric power W1 is subtracted from the maximum source electric power W0max of the battery 31 (step S126). The controller 32 then controls the driving state of the second energy generator 51 to supply the second driving electric power W2 to the second energy generator 51 (step S127). The supply of the second driving electric power W2 is started at the time of the switch of the supply state of the first driving electric power W1 to the constant voltage control (the time tc in FIG. 8) or immediately after the switch. That is, the supply of the second driving electric power W2 to the second energy generator 51 is started in response to the switch of the supply state of the first driving electric power W1 to the constant voltage control.

In step S127, the second driving electric power W2 is supplied to the second energy generator 51 in a state where the second driving electric power W2 is less than or equal to the calculated surplus electric power Q1. That is, at and after the start of the supply of the second driving electric power W2, the controller 32 controls the second driving electric power W2 in a range in which the second driving electric power W2 is less than or equal to the surplus electric power Q1. For example, in FIG. 8, an electric power value W2d of the second driving electric power W2 is less than or equal to an electric power value Q1d of the surplus electric power Q1 at a time td. As described above, at and after the start of the supply of the second driving electric power W2, the second driving electric power W2 is kept less than or equal to the surplus electric power Q1 in which the first driving electric power W1 is subtracted from the maximum source electric power W0max continuously with time. Thus, the sum of the first driving electric power W1 and the second driving electric power W2 that are supplied per unit time is kept less than or equal to the maximum source electric power W0max of the battery 31 continuously with time. When the treatment using the energy is continued (step S128—No), steps S125 to S127 are repeated with time.

As described above, in the present modification as well as in the first embodiment, the sum of the first driving electric power W1 and the second driving electric power W2 that are supplied per unit time is kept less than or equal to the maximum source electric power W0max of the battery 31 continuously with time even in a state where both the first driving electric power W1 and the second driving electric power W2 are supplied. Thus, as in the first embodiment, the battery 31 which outputs low source electric power (electric capacity) W0 can be used in the energy treatment instrument 1.

Second Embodiment

Figure 12:
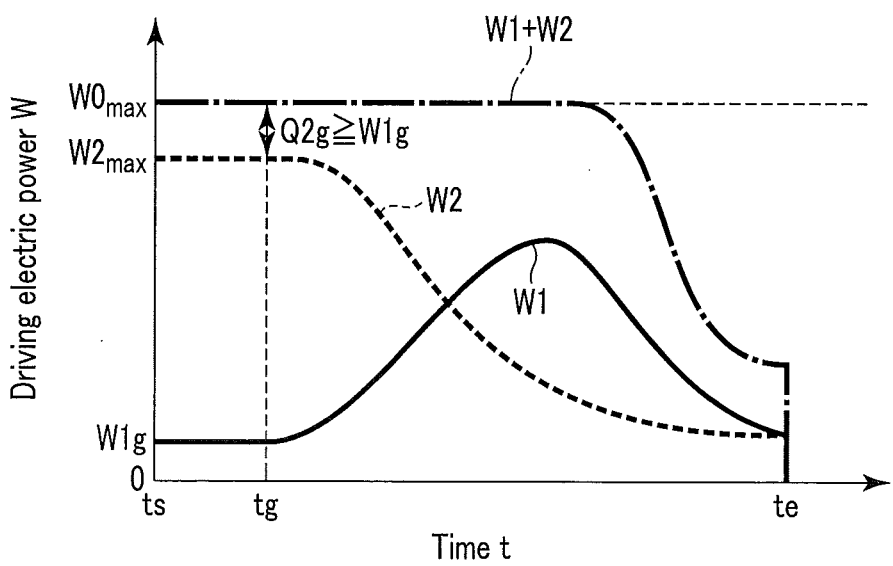
FIG. 12 is a schematic diagram showing changes of the first driving electric power and the second driving electric power with time in a state where the controller controls in the second energy mode according to the second embodiment.

Next, a second embodiment of the present invention is described with reference to FIG. 9 to and FIG. 12. The second embodiment is the following modification of the configuration according to the first embodiment. The same parts as those in the first embodiment are denoted with the same reference marks, and are not described.

Figure 9:
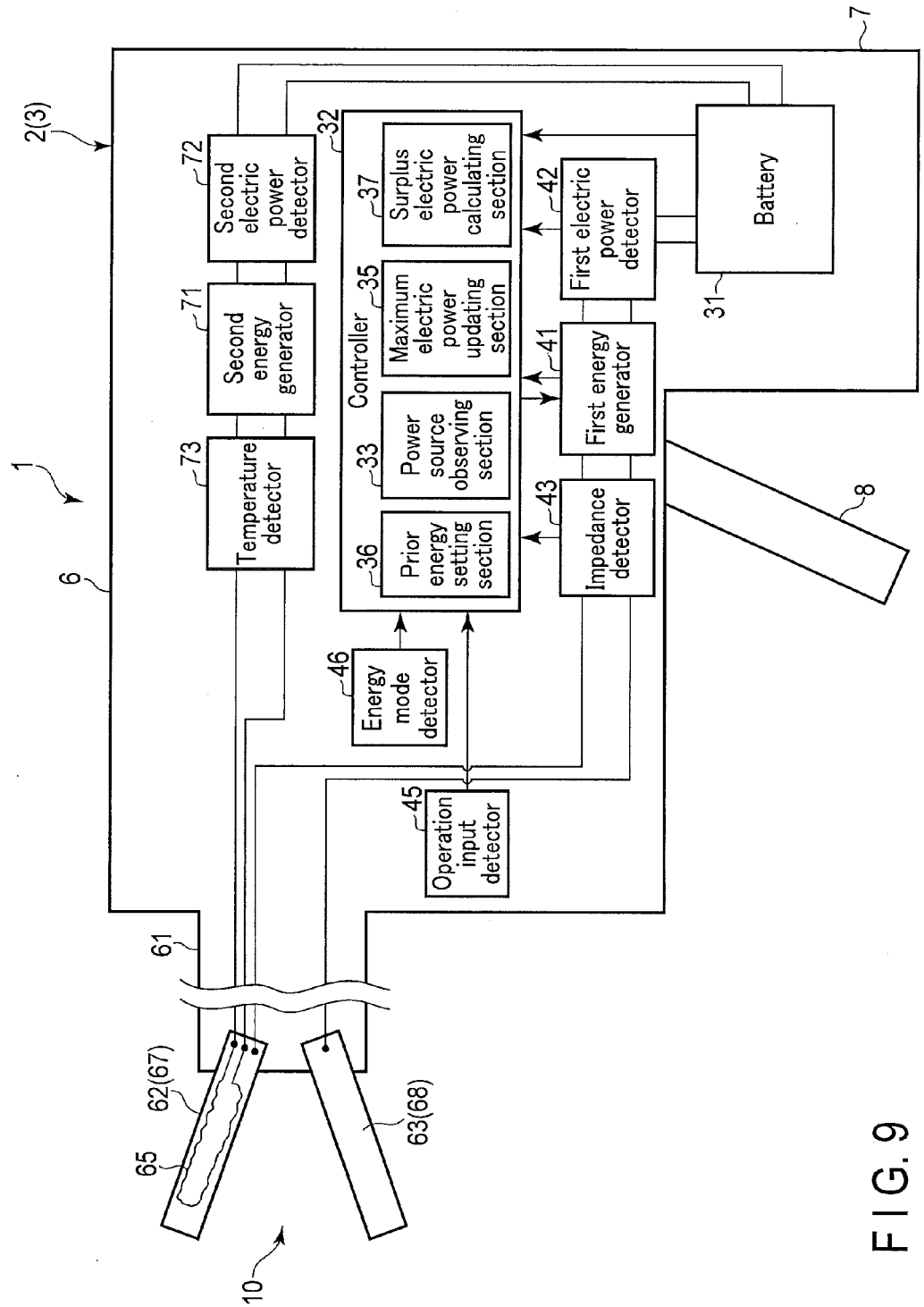
FIG. 9 is a schematic diagram showing the configuration of the energy treatment instrument according to a second embodiment.

FIG. 9 is a diagram showing the configuration of the energy treatment instrument 1 according to the present embodiment. In the present embodiment, heat (heat generating electric power P'2) is used as the second energy instead of the ultrasonic vibration (vibration generating electric power P2). However, in the present modification as well, the high-frequency electric power P1 is used as the first energy in the treatment. In the present modification, no ultrasonic vibration needs to be generated, so that the transducer assembly 5 is not provided, and the holding unit 2 is formed from the handle assembly 3 alone. In the holding unit 2 (the handle assembly 3), the case body portion 6, the fixed handle 7, and the movable handle 8 are provided as in the first embodiment.

In the present modification, a shaft 61 is coupled to the case body portion 6 from the distal side. A first jaw 62 and a second jaw 63 are coupled to the distal portion of the shaft 61. The first jaw 62 and the second jaw 63 are openable and closable relative to each other. When the movable handle 8 is closed relative to the fixed handle 7, the first jaw 62 and the second jaw 63 close relative to each other, and the treated target can be grasped between the first jaw 62 and the second jaw 63. One of the first jaw 62 and the second jaw 63 may be fixed to the shaft 61, and the other may be rotatable relative to the shaft 61, or both the jaws may be rotatable relative to the shaft 61. In the present embodiment, the treatment portion (end effector) 10 which treats a treated target such as a living tissue by use of energies (the high-frequency electric power P1 and heat in the present embodiment) is formed by the first jaw 62 and the second jaw 63.

As in the first embodiment, the operation input detector 45, the energy mode detector 46, and the controller 32 are provided inside the holding unit 2. As in the first embodiment, the controller 32 includes the power source observing section 33, the maximum electric power updating section 35, the prior energy setting section 36, and the surplus electric power calculating section 37. As in the first embodiment, the first energy generator 41, the first electric power detector 42, and the impedance detector 43 are provided inside the holding unit 2. As in the first embodiment, when the first driving electric power W1 is supplied to the first energy generator 41, the high-frequency electric power P1 is generated as the first energy. The first electric power detector 42 detects the supplied first driving electric power W1 with time.

In the present embodiment, a first electrode portion (electrode portion) 67 is provided in the first jaw 62, and a second electrode portion (electrode portion) 68 is provided in the second jaw 63. The generated high-frequency electric power P1 is supplied to the first electrode portion 67 and the second electrode portion 68, and the high-frequency voltage (electric potential difference) V1 is generated between the first electrode portion 67 and the second electrode portion 68. Accordingly, the high-frequency electric current I1 flows through the treated target grasped between the first jaw 62 and the second jaw 63, and the treated target is coagulated by the high-frequency electric current I1 as in the first embodiment. As in the first embodiment, the impedance detector 43 detects the impedance Z1 (i.e. the impedance of the treated target) for the high-frequency electric current I1 with time.

In the present embodiment, a second energy generator 71, a second electric power detector 72, and a temperature detector 73 are provided inside the holding unit 2. The second energy generator 71 is formed from, for example, a driving circuit including an amplifier circuit, and is connected to the controller 32 via an interface such as a bus. The driving state of the second energy generator 71 is controlled by the controller 32, and the driving state of the second energy generator 71 is fed back to the controller 32. The second electric power detector 72 and the temperature detector 73 are formed from, for example, detecting circuits.

In the present embodiment, the second driving electric power W2 is supplied to the second energy generator 71 due to the source electric power W0 output from the battery 31. The second energy generator 71 is driven by the second driving electric power W2, and the heat generating electric power P'2 is generated as second energy. The electric power value (degree) of the second driving electric power W2 changes in response to the driving state of the second energy generator 71. The second electric power detector 72 detects the second driving electric power W2 with time. A detection result in the second electric power detector 72 is transmitted to the controller 32 via an interface such as a bus. The electric power value of the heat generating electric power P'2 which is the second energy changes in response to the electric power value of the second driving electric power W2, and when the second driving electric power W2 is constant with time, the heat generating electric power P'2 is also constant with time. As the second driving electric power W2 increases, the heat generating electric power P'2 also increases.

In the present embodiment, a heating element 65 such as a heater is provided in the first jaw 62. When the generated heat generating electric power P'2 is supplied to the heating element 65, the heating element 65 generates heat. The generated heat is transmitted to the treated target grasped between the first jaw 62 and the second jaw 63 through the first jaw 62. That is, the generated heat is transmitted to the treatment portion 10. The treated target is coagulated and cut at the same time by the heat. In general, cutting performance by heat is higher than cutting performance by the high-frequency electric current because the treated target can be more easily brought to a high temperature by heat than by the high-frequency electric current. The heating element 65 has only to be provided in the treatment portion 10, and may be provided in, for example, the second jaw 63. The temperature detector 73 detects a temperature T (i.e. electric resistance) of the heating element 65 to which the heat generating electric power P'2 is supplied. A detection result in the temperature detector 73 is transmitted to the controller 32 via an interface such as a bus.

Figure 10:
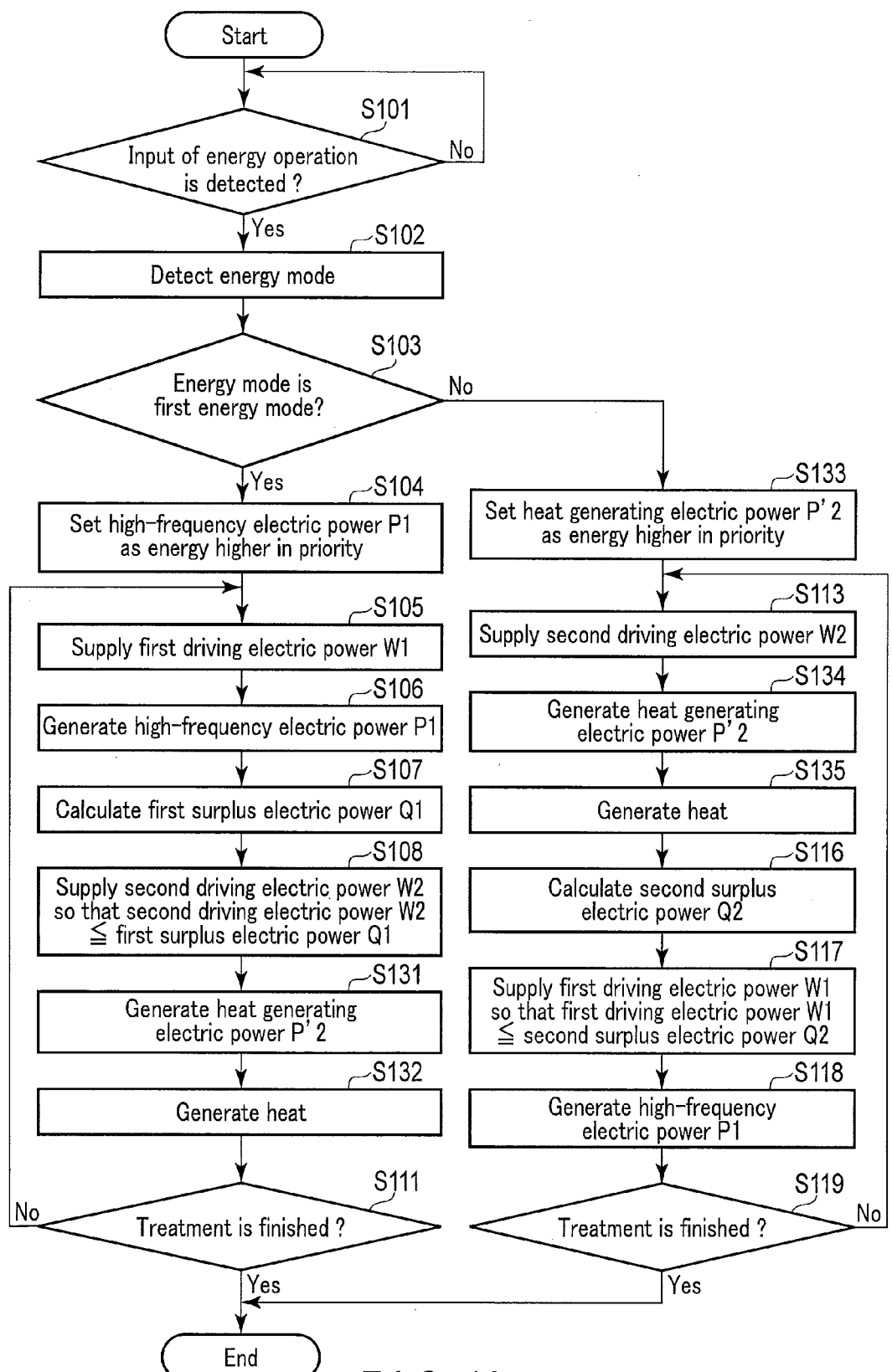
FIG. 10 is a flowchart showing processing in the energy treatment instrument in a state where the energies for use in the treatment are supplied to the treatment portion according to the second embodiment.
Figure 11:
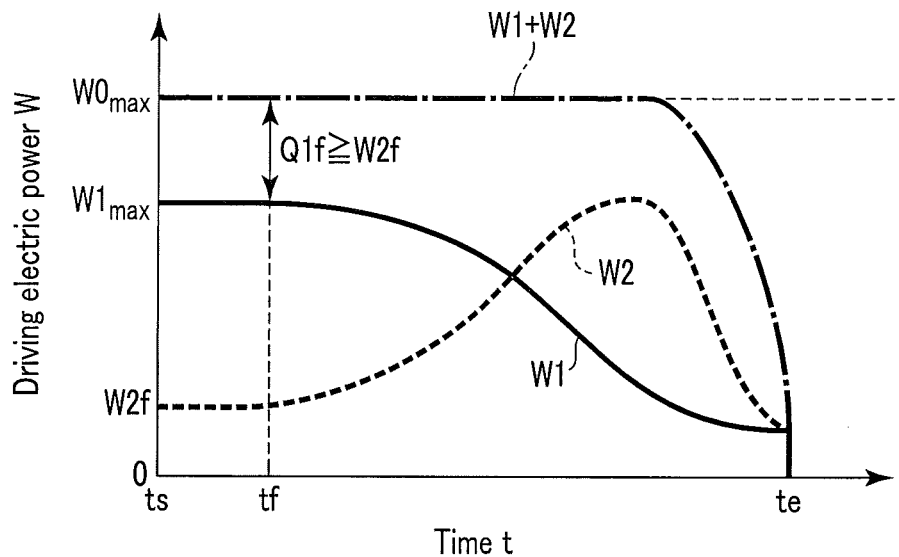
FIG. 11 is a schematic diagram showing changes of the first driving electric power and the second driving electric power with time in a state where the controller controls in the first energy mode according to the second embodiment.

FIG. 10 is a flowchart showing processing in the energy treatment instrument 1 in a state where the energies (the first energy and the second energy) for use in the treatment are supplied to the treatment portion 10. FIG. 11 is a diagram showing changes of the first driving electric power W1 and the second driving electric power W2 with time in a state where the controller 32 controls in the first energy mode. FIG. 12 is a diagram showing changes of the first driving electric power W1 and the second driving electric power W2 with time in a state where the controller 32 controls in the second energy mode. In FIG. 11 and FIG. 12, the time t is indicated on the abscissa axis, the supply start time of the first driving electric power W1 and the second driving electric power W2 is indicated by ts, and the supply stop time of the first driving electric power W1 and the second driving electric power W2 is indicated by te. The time from ts to te is about 2 to 5 seconds. Moreover, in FIG. 11 and FIG. 12, the driving electric powers (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

As shown in FIG. 10, in the present embodiment as well as in the first embodiment, when the operation input detector 45 detects the input of an energy operation (step S101—Yes), the energy mode detector 46 detects an energy mode (step S102). When the detected energy mode is the first energy mode (step S103—Yes), the prior energy setting section 36 sets the high-frequency electric power P1 which is the first energy as energy higher in priority in the treatment with the treatment portion 10 (step S104). Thus, the first driving electric power W1 that is supplied to the first energy generator 41 is prior driving electric power.

In the first energy mode, as in the first embodiment, the controller 32 controls the driving state of the first energy generator 41 to supply the first driving electric power W1 to the first energy generator 41 (step S105). In this instance, the first driving electric power W1 is lower than the maximum source electric power W0max of the battery 31. The first energy generator 41 generates the high-frequency electric power P1 as the first energy by the supply of the first driving electric power W1 (step S106). The high-frequency electric power P1 is then supplied to the first electrode portion 67 and the second electrode portion 68 of the treatment portion 10, and the treated target is treated by the high-frequency electric current I1 as has been described above in the first embodiment. In the present embodiment as well as in the first embodiment, in the first energy mode, the first driving electric power W1 is controlled so that the load characteristics (change characteristics) of the first driving electric power W1 for the impedance Z1 may be similar to the load characteristics shown in FIG. 4 on the basis of the detection result of the impedance (high-frequency impedance) Z1 in the impedance detector 43. Therefore, the controller 32 adjusts the first driving electric power W1 by one of the constant current control, the constant electric power control, and the constant voltage control on the basis of the detection result of the impedance $Z1$ so that the first driving electric power $W1$ may be lower.

As shown in FIG. 10, when the high-frequency electric power $P1$ is generated by the first driving electric power $W1$ (step S106), the surplus electric power calculating section 37 calculates, with time, the first surplus electric power $Q1$ in which the first driving electric power $W1$ that is the prior driving electric power is subtracted from the maximum source electric power $W0max$ of the battery 31 as in the first energy mode according to the first embodiment (step S107). The controller 32 then controls the driving state of the second energy generator 71 on the basis of the calculated first surplus electric power $Q1$, and supplies the second driving electric power $W2$ to the second energy generator 71 (step S108). By the supply of the second driving electric power $W2$, the second energy generator 71 generates the heat generating electric power $P'2$ as the second energy (step S131). The heat generating electric power $P'2$ is then supplied to the heating element 65, and the heating element 65 generates heat (step S132). When the heat is transmitted to the first jaw 62 of the treatment portion 10 as the second energy, the treated target is coagulated and cut at the same time by the heat. In this instance, the temperature detector 73 detects the temperature T of the heating element 65 with time.

In the present embodiment as well, in step S108, the second driving electric power $W2$ is supplied to the second energy generator 71 in a state where the second driving electric power $W2$ is less than or equal to the calculated first surplus electric power $Q1$. That is, in the present embodiment as well, in the first energy mode in which the first driving electric power $W1$ is the prior driving electric power, Equation (2) is satisfied, and Equation (3) is satisfied. Therefore, in the first energy mode, the sum $(W1+W2)$ of the first driving electric power $W1$ and the second driving electric power $W2$ that are supplied per unit time is less than or equal to the maximum source electric power $W0max$ of the battery (electric power source) 31. When the treatment in the first energy mode is continued (step S111—No), steps S105 to S108, S131, and S132 are repeated with time.

In the present embodiment as well as in the first embodiment, when a certain period of time passes since the supply start time ts of the first driving electric power $W1$ and the second driving electric power $W2$, the impedance $Z1$ increases to a range in which the constant voltage control to keep the high-frequency voltage $V1$ constant with time is performed. Therefore, as shown in FIG. 11, in the first energy mode, when a certain period of time passes since the supply start time ts, a switch is made from the constant electric power control to keep the first driving electric power (the high-frequency electric power $P1$) constant with time to the aforementioned constant voltage control. Due to the switch of the control of the first driving electric power $W1$ to the constant voltage control, the first driving electric power $W1$ decreases with time.

In the first energy mode, the first driving electric power $W1$ to generate the high-frequency electric power $P1$ which is the prior energy is supplied by priority. Thus, in the first energy mode, the high-frequency electric power $P1$ is generated by priority over the heat generating electric power $P'2$. Therefore, in the first energy mode, a treatment higher in coagulation performance than in cutting performance is conducted by the treatment portion 10.

In the first energy mode, the second driving electric power $W2$ is supplied to the second energy generator 71 in a range less than or equal to the first surplus electric power $Q1$ in which the first driving electric power $W1$ is subtracted from the maximum source electric power $W0max$ of the battery 31. Because the second driving electric power $W2$ is kept less than or equal to the first surplus electric power $Q1$ continuously with time, the sum of the first driving electric power $W1$ and the second driving electric power $W2$ that are supplied per unit time is kept less than or equal to the maximum source electric power $W0max$ of the battery 31 continuously with time in the first energy mode in the present embodiment as well.

In the first energy mode according to the present embodiment, the first driving electric power $W1$ is supplied at the first maximum driving electric power $W1max$ which is the maximum value, for example, at a time tf. However, at the time tf, an electric power value $W2f$ of the second driving electric power $W2$ is less than or equal to an electric power value $Q1f$ of the first surplus electric power $Q1$. Thus, even at the time tf when the first driving electric power $W1$ is the first maximum driving electric power $W1max$ which is the maximum value, the sum of the first driving electric power $W1$ and the second driving electric power $W2$ is less than or equal to the maximum source electric power $W0max$ of the battery 31.

As shown in FIG. 10, when the detected energy mode is the second energy mode (step S103—No), the prior energy setting section 36 sets the heat generating electric power $P'2$ and the heat which are the second energies as energies higher in priority in the treatment with the treatment portion 10 (step S133). Thus, the second driving electric power $W2$ that is supplied to the second energy generator 71 is prior driving electric power.

In the second energy mode, as in the first embodiment, the controller 32 controls the driving state of the second energy generator 71 to supply the second driving electric power $W2$ to the second energy generator 71 (step S113). In this instance, the second driving electric power $W2$ is lower than the maximum source electric power $W0max$ of the battery 31. The second energy generator 71 generates the heat generating electric power $P'2$ as the second energy by the supply of the second driving electric power $W2$ (step S134). The heat generating electric power $P'2$ is then supplied to the heating element 65, and the heating element 65 generates heat (step S135). When the heat is transmitted to the first jaw 62 of the treatment portion 10 as the second energy, the treated target is coagulated and cut at the same time by the heat.

In the second energy mode in which the heat is the prior energy, the controller 32 controls the second energy generator 71 on the basis of the detected temperature T of the heating element 65. When the temperature T of the heating element 65 is lower than a desired temperature (set temperature) $T0$ (i.e. when the temperature is low), the second driving electric power $W2$ (i.e. the heat generating electric power $P'2$) increases, and for example, the constant electric power control to keep the second driving electric power $W2$ (the heat generating electric power $P'2$) at a high electric power value constant with time is performed. When the temperature T of the heating element 65 becomes less than or equal to the desired temperature $T0$, the second driving electric power $W2$ is adjusted so that the temperature T of the heating element 65 will be the desired temperature $T0$. That is, the controller 32 performs constant temperature control to keep the temperature T of the heating element 65 at the desired temperature $T0$ constant with time. In a state where the constant temperature control to keep the temperature T at the desired temperature $T0$ is performed, the second driving electric power $W2$ that is supplied to the second energy generator 71 is lower than when the temperature T of the heating element 65 is lower than the desired temperature T0. The desired temperature T0 is set to a certain temperature ranging, for example, from 250° C. to 350° C.

As shown in FIG. 10, when the heat is generated by the second driving electric power W2 (step S135), the surplus electric power calculating section 37 calculates, with time, the second surplus electric power Q2 in which the second driving electric power W2 that is the prior driving electric power is subtracted from the maximum source electric power W0max of the battery 31 (step S116). As in the first embodiment, the controller 32 then controls the driving state of the first energy generator 41 on the basis of the calculated second surplus electric power Q2, and supplies the first driving electric power W1 to the first energy generator 41 (step S117). By the supply of the first driving electric power W1, the first energy generator 41 generates the high-frequency electric power P1 as the first energy (step S118). The high-frequency electric power P1 is then supplied to the first electrode portion 67 and the second electrode portion 68 of the treatment portion 10, and the treated target is degenerated and coagulated as described above.

In the present embodiment as well, in step S117, the first driving electric power W1 is supplied to the first energy generator 41 in a state where the first driving electric power W1 is less than or equal to the calculated second surplus electric power Q2. That is, in the present embodiment as well, in the second energy mode in which the second driving electric power W2 is the prior driving electric power, Equation (5) is satisfied, and Equation (3) is satisfied. Therefore, in the second energy mode as well, the sum (W1+W2) of the first driving electric power W1 and the second driving electric power W2 that are supplied per unit time is less than or equal to the maximum source electric power W0max of the battery (electric power source) 31. When the treatment in the second energy mode is continued (step S119—No), steps S113, S134, S135, and S116 to S118 are repeated with time.

In the second energy mode, when a certain period of time passes since the supply start time is of the first driving electric power W1 and the second driving electric power W2, the temperature T of the heating element 65 reaches the desired temperature T0, and the control of the second driving electric power W2 is switched to the aforementioned constant temperature control. Due to the switch of the control of the second driving electric power W2 to the constant temperature control, the second driving electric power W2 decreases with time as shown in FIG. 12.

In the second energy mode, the second driving electric power W2 to generate the heat generating electric power P'2 which is the prior energy is supplied by priority. Thus, in the second energy mode, the heat generating electric power P'2 (heat) is generated by priority over the high-frequency electric power P1. Therefore, in the second energy mode, a treatment higher in cutting performance than in coagulation performance is conducted by the treatment portion 10.

In the second energy mode, the first driving electric power W1 is supplied to the first energy generator 41 in a range less than or equal to the second surplus electric power Q2 in which the second driving electric power W2 is subtracted from the maximum source electric power W0max of the battery 31. Because the first driving electric power W1 is kept less than or equal to the second surplus electric power Q2 continuously with time, the sum of the first driving electric power W1 and the second driving electric power W2 that are supplied per unit time is kept less than or equal to the maximum source electric power W0max of the battery 31 continuously with time in the second energy mode.

In the second energy mode according to the present embodiment, the second driving electric power W2 is supplied at the second maximum driving electric power W2max which is the maximum value, for example, at a time tg. However, at the time tg, an electric power value Wig of the first driving electric power W1 is less than or equal to an electric power value Q2g of the second surplus electric power Q2. Thus, even at the time tg when the second driving electric power W2 is the second maximum driving electric power W2max which is the maximum value, the sum of the first driving electric power W1 and the second driving electric power W2 is less than or equal to the maximum source electric power W0max of the battery 31.

In the present embodiment as well, the maximum source electric power W0max of the battery 31 is lower than the sum of the first maximum driving electric power W1max which is the maximum value of the first driving electric power W1 and the second maximum driving electric power W2max which is the maximum value of the second driving electric power W2, and Equation (6) above is satisfied. However, in the present embodiment, the first driving electric power W1 and the second driving electric power W2 are controlled as described above, so that even when the sum of the first maximum driving electric power W1max and the second maximum driving electric power W2max is higher than the maximum source electric power W0max of the battery 31, the sum of the first driving electric power W1 and the second driving electric power W2 that are supplied per unit time is kept less than or equal to the maximum source electric power W0max of the battery 31 continuously with time in both the first energy mode and the second energy mode. Thus, the battery 31 which outputs low source electric power (electric capacity) W0 can be used in the energy treatment instrument 1. That is, the maximum source electric power W0max of the battery 31 which is the electric power source used in the energy treatment instrument 1 can be reduced. Therefore, it is possible to provide the energy treatment instrument 1 which suitably conducts a treatment by simultaneously using energies (the high-frequency electric power P1 and the heat in the present embodiment) without the increase of the source electric power W0 output from the battery 31, and functions and advantageous effects similar to those in the first embodiment are provided.

Modifications of the Second Embodiment

Next, a first modification of the second embodiment shown in FIG. 13 is described. In the present modification as well as in the first modification of the first embodiment, the prior energy setting section 36 is not provided, and the prior energy higher in priority is not set. FIG. 13 is a diagram showing changes of the first driving electric power W1 and the second driving electric power W2 with time in a state where the energy or the energies is/are supplied to the treatment portion. In FIG. 13, the time t is indicated on the abscissa axis, and the driving electric powers W (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

In the present modification as well as in the first modification of the first embodiment, the first driving electric power W1 and the second driving electric power W2 are supplied. That is, to describe with reference to FIG. 7, in the present modification as well, when the operation input detector 45 detects the input of an energy operation (step S121—Yes), the controller 32 controls the driving state of the first energy generator 41 to supply the first driving electric power W1 to the first energy generator 41 (step S122). Accordingly, the high-frequency electric power P1 is generated as the first energy, and the treated target is coagulated by the high-frequency electric current I1 as described above. In the present modification as well, the first driving electric power W1 is controlled so that the load characteristics of the first driving electric power W1 for the impedance Z1 may be similar to the load characteristics shown in FIG. 4 on the basis of the detection result of the impedance (high-frequency impedance) Z1. Therefore, the controller 32 adjusts the first driving electric power W1 by one of the constant current control, the constant electric power control, and the constant voltage control on the basis of the detection result of the impedance Z1 so that the first driving electric power W1 may be lower.

In the present modification as well, even if the supply of the first driving electric power W1 is started, the controller 32 controls the driving state of the second energy generator 71 to keep the supply of the second driving electric power W2 to the second energy generator 71 stopped (step S123). Therefore, at the start of the treatment with the treatment portion 10, the controller 32 starts the supply of the first driving electric power W1 to the first energy generator 41 without supplying the second driving electric power W2 to the second energy generator 71. In this instance, as shown in FIG. 13, the first driving electric power W1 is supplied in a state where the electric power value of the first driving electric power W1 is the same as the maximum source electric power W0max of the battery 31. However, the second driving electric power W2 is not supplied, so that as in the previously described embodiments and others, the sum of the first driving electric power W1 and the second driving electric power W2 that are supplied per unit time is kept less than or equal to the maximum source electric power W0max of the battery (actually, the same as the maximum source electric power W0max) continuously with time, and Equation (3) above is satisfied. In FIG. 13, the supply start time of the first driving electric power W1 is indicated by ts, and the supply stop time of the first driving electric power W1 and the second driving electric power W2 is indicated by te.

The second driving electric power W2 is not supplied and the first driving electric power W1 alone is supplied, so that when a certain period of time passes since the supply start time ts of the first driving electric power W1, the impedance (high-frequency impedance) Z1 increases to a range in which the constant voltage control to keep the high-frequency voltage V1 constant with time is performed. That is, the supply state of the first driving electric power W1 is switched by the controller 32 from the constant electric power control to keep the first driving electric power W1 constant with time to the constant voltage control, in response to the change of the impedance Z1 with time. Due to the switch to the constant voltage control, the electric power value of the first driving electric power W1 starts to decrease (from the maximum source electric power W0max in the present modification). When a switch to the constant voltage control is not made (step S124—No), steps S122 and S123 are repeated with time until a switch to the constant voltage control is made (i.e. until the first driving electric power W1 starts to decrease). In FIG. 13, the supply state of the first driving electric power W1 is switched from the constant electric power control to the constant voltage control at a time tn. In the present modification, the electric power value (W1p in FIG. 4) of the first driving electric power W1 under the constant electric power control is the same as the maximum source electric power W0max of the battery 31.

When the supply state of the first driving electric power W1 is switched to the constant voltage control (step S124—Yes), the controller 32 maintains the supply of the first driving electric power W1 (step S125), and the surplus electric power calculating section 37 calculates, with time, the surplus electric power (first surplus electric power) Q1 in which the first driving electric power W1 is subtracted from the maximum source electric power W0max of the battery 31 (step S126). The controller 32 then controls the driving state of the second energy generator 71 to supply the second driving electric power W2 to the second energy generator 71 (step S127). The supply of the second driving electric power W2 is started at the time of the switch of the supply state of the first driving electric power W1 to the constant voltage control (the time to in FIG. 13) or immediately after the switch. That is, the supply of the second driving electric power W2 to the second energy generator 71 is started in response to the switch of the supply state of the first driving electric power W1 to the constant voltage control.

In step S127, the second driving electric power W2 is supplied to the second energy generator 71 in a state where the second driving electric power W2 is less than or equal to the calculated surplus electric power Q1. That is, at and after the start of the supply of the second driving electric power W2, the controller 32 controls the second driving electric power W2 in a range in which the second driving electric power W2 is less than or equal to the surplus electric power Q1. Thus, the sum of the first driving electric power W1 and the second driving electric power W2 that are supplied per unit time is kept less than or equal to the maximum source electric power W0max of the battery 31 continuously with time. In this instance, when the temperature T of the heating element 65 has reached the desired temperature T0, the second driving electric power W2 is controlled under the aforementioned constant temperature control to keep the heating element 65 constant at the desired temperature T0 with time. When the treatment using the energy is continued (step S128—No), steps S125 to S127 are repeated with time.

As described above, in the present modification as well as in the previously described embodiments and others, the sum of the first driving electric power W1 and the second driving electric power W2 that are supplied per unit time is kept less than or equal to the maximum source electric power W0max of the battery 31 continuously with time even in a state where both the first driving electric power W1 and the second driving electric power W2 are supplied. Thus, as in the previously described embodiments and others, the battery 31 which outputs low source electric power (electric capacity) W0 can be used in the energy treatment instrument 1.

At the start of the treatment, the first driving electric power W1 alone is first supplied, and the high-frequency electric power P1 alone is supplied. The high-frequency electric current I1 is then passed through the treated target, and heat is generated in the heating element 65 in a state where the treated target has risen to a certain degree of temperature due to the high-frequency electric current I1. Thus, the treated target (the heating element 65) can be raised to the desired temperature T0 in a short time without the increase of calorific value in the heating element 65, that is, without the increase of the second driving electric power W2 (the heat generating electric power P'2).

Next, a second modification of the second embodiment shown in FIG. 14 to FIG. 17 is described. In the present modification as well, the prior energy setting section 36 is not provided, and the prior energy higher in priority is not set. FIG. 14 is a flowchart showing processing in the energy treatment instrument 1 in a state where the energy or the energies for use in the treatment is/are supplied to the treatment portion 10. FIG. 15 is a diagram showing changes of the first driving electric power W1 and the second driving electric power W2 with time in a state where the energy or the energies is/are supplied to the treatment portion 10. In FIG. 15, the time t is indicated on the abscissa axis, and the driving electric powers W (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line. FIG. 16 is a diagram showing a change of the impedance (high-frequency impedance) Z1 for the high-frequency electric current I1 with time in a state where the energy or the energies is/are supplied to the treatment portion 10. FIG. 17 is a diagram showing a change of the temperature T of the heating element 65 with time in a state where the energy or the energies is/are supplied to the treatment portion 10. In FIG. 16, the time t is indicated on the abscissa axis, and the impedance Z1 is indicated on the ordinate axis. In FIG. 17, the time t is indicated on the abscissa axis, and the temperature T is indicated on the ordinate axis.

As shown in FIG. 14, in the present modification as well as in the first modification of the second embodiment, when the operation input detector 45 detects the input of an energy operation (step S141—Yes), the controller 32 controls the driving state of the first energy generator 41 to supply the first driving electric power W1 to the first energy generator 41 (step S142). The first energy generator 41 generates the high-frequency electric power P1 as the first energy by the supply of the first driving electric power W1, and the treated target is coagulated by the high-frequency electric current I1 as described above. In the present modification as well, the first driving electric power W1 is controlled so that the load characteristics of the first driving electric power W1 for the impedance Z1 may be similar to the load characteristics shown in FIG. 4 on the basis of the detection result of the impedance (high-frequency impedance) Z1. Therefore, the controller 32 adjusts the first driving electric power W1 by one of the constant current control, the constant electric power control, and the constant voltage control on the basis of the detection result of the impedance Z1 so that the first driving electric power W1 may be lower.

Even if the supply of the first driving electric power W1 is started, the controller 32 controls the driving state of the second energy generator 71 to keep the supply of the second driving electric power W2 to the second energy generator 71 stopped (step S143). Therefore, at the start of the treatment with the treatment portion 10, the controller 32 starts the supply of the first driving electric power W1 to the first energy generator 41 without supplying the second driving electric power W2 to the second energy generator 71. In this instance, as shown in FIG. 15, the first driving electric power W1 is supplied in a state where the electric power value of the first driving electric power W1 is the same as the maximum source electric power W0max of the battery 31. However, the second driving electric power W2 is not supplied, so that as in the previously described embodiments and others, the sum of the first driving electric power W1 and the second driving electric power W2 that are supplied per unit time is kept less than or equal to the maximum source electric power W0max of the battery 31 (actually, the same as the maximum source electric power W0max) continuously with time. In FIG. 15 to FIG. 17, the supply start time of the first driving electric power W1 is indicated by ts, and the supply stop time of the first driving electric power W1 and the second driving electric power W2 is indicated by te.

The second driving electric power W2 is not supplied and the first driving electric power W1 alone is supplied, so that when a certain period of time passes since the supply start time is of the first driving electric power W1, the impedance (high-frequency impedance) Z1 increases to a range in which the constant voltage control to keep the high-frequency voltage V1 constant with time is performed. That is, the supply state of the first driving electric power W1 is switched by the controller 32 from the constant electric power control to keep the first driving electric power W1 constant with time to the constant voltage control, in response to the change of the impedance Z1 with time. Due to the switch to the constant voltage control, the electric power value of the first driving electric power W1 starts to decrease (from the maximum source electric power W0max in the present modification). When the first driving electric power W1 does not start to decrease (step S144—No), steps S142 and S143 are repeated with time until the first driving electric power W1 starts to decrease (i.e. until a switch to the constant voltage control is made). In FIG. 15 and FIG. 16, at a time t ti, the impedance Z1 becomes higher than a threshold Z1*th* to switch to the constant voltage control, and the supply state of the first driving electric power W1 is switched from the constant electric power control to the constant voltage control, so that the first driving electric power W1 starts to decrease. In the present modification, the electric power value (W1*p* in FIG. 4) of the first driving electric power W1 under the constant electric power control is the same as the maximum source electric power W0max of the battery 31. The threshold Z1*th* of the impedance Z1, at which the switch to the constant voltage control is performed, is higher than an impedance value Z1*s* of the impedance Z1 at the supply start time is of the first driving electric power W1.

When the first driving electric power W1 starts to decrease (step S144—Yes), the controller 32 controls the driving state of the first energy generator 41 to stop the supply of the first driving electric power W1 to the first energy generator 41 (step S145). The controller 32 then controls the driving state of the second energy generator 71 to supply the second driving electric power W2 to the second energy generator 71 (step S146). The supply of the first driving electric power W1 to the first energy generator 41 is stopped and the supply of the second driving electric power W2 to the second energy generator 71 is started at the start of the decrease of the first driving electric power W1 (a time ti in FIG. 15) or immediately after the start of the decrease. Therefore, at and after the start of the supply of the first driving electric power W1, the supply of the first driving electric power W1 to the first energy generator 41 is stopped and the supply of the second driving electric power W2 to the second energy generator 71 is started in response to the start of the decrease of the first driving electric power W1 resulting from the change of the impedance Z1 for the high-frequency electric current I1 with time.

As shown in FIG. 17, at the start of the supply of the second driving electric power W2 (immediately after the start of the decrease of the first driving electric power W1), the temperature T of the heating element 65 (the treated target) is substantially the same as the temperature T (a temperature Ti in FIG. 17) at the start of the decrease of the first driving electric power W1, and is lower than the desired temperature T0. Thus, as shown in FIG. 15 and FIG. 17, for a certain period of time since the start of the supply the second driving electric power W2, the second driving electric power W2 is controlled under the constant electric power control, and the second driving electric power W2 is supplied in a state where the electric power value of the second driving electric power W2 is the same as the maximum source electric power W0max of the battery 31. In this instance, the first driving electric power W1 is not supplied, so that as in the previously described embodiments and others, the sum of the first driving electric power W1 and the second driving electric power W2 that are supplied per unit time is kept less than or equal to the maximum source electric power W0max of the battery 31 (actually, the same as the maximum source electric power W0max) continuously with time. As shown in FIG. 17, the temperature of the treated target (the heating element 65) rises due to the flow of the high-frequency electric current I1 through the treated target, so that the temperature T (the temperature Ti in FIG. 17) at the decrease start time ti of the first driving electric power W1 is higher than the temperature T (a temperature Ts in FIG. 17) of the heating element at the supply start time ts of the first driving electric power W1.

When a certain period of time passes since the start of the supply of the second driving electric power W2, the temperature T of the heating element 65 reaches the desired temperature T0, and the constant temperature control to keep the temperature T of the heating element 65 constant at the desired temperature T0 with time is performed. That is, at and after the start of the supply of the second driving electric power W2, the supply state of the second driving electric power W2 is switched by the controller 32 from the constant electric power control to keep the second driving electric power W2 constant with time to the constant temperature control, in response to the change of the temperature T of the heating element 65 with time. Due to the switch to the constant temperature control, the second driving electric power W2 starts to decrease (from the maximum source electric power W0max in the present modification). When the second driving electric power W2 is not switched to the constant temperature control (step S147—No), steps S145 and S146 are repeated with time until the second driving electric power W2 is switched to the constant temperature control (i.e. until the temperature T reaches the desired temperature T0). In FIG. 15 to FIG. 17, at a time tj, the temperature T of the heating element reaches the desired temperature T0, and the supply state of the second driving electric power W2 is switched from the constant electric power control to the constant temperature control.

When the supply state of the second driving electric power W2 is switched to the constant temperature control (step S147—Yes), the controller 32 maintains the supply of the second driving electric power W2 (step S148), and the surplus electric power calculating section 37 calculates, with time, the surplus electric power (second surplus electric power) Q2 in which the second driving electric power W2 is subtracted from the maximum source electric power W0max of the battery 31 (step S149). The controller 32 then controls the driving state of the first energy generator 41 to supply the first driving electric power W1 to the first energy generator 41 (step S150). The supply of the first driving electric power W1 is started at the time of the switch of the supply state of the second driving electric power W2 to the constant temperature control (the time tj in FIG. 15) or immediately after the switch. That is, the supply of the first driving electric power W1 to the first energy generator 41 is restarted in response to the switch of the supply state of the second driving electric power W2 to the constant temperature control.

In step S150, the first driving electric power W1 is supplied to the first energy generator 41 in a state where the first driving electric power W1 is less than or equal to the calculated surplus electric power Q2. That is, at and after the restart of the supply of the first driving electric power W1, the controller 32 controls the first driving electric power W1 in a range in which the first driving electric power W1 is less than or equal to the surplus electric power Q2. Thus, the sum of the first driving electric power W1 and the second driving electric power W2 that are supplied per unit time is kept less than or equal to the maximum source electric power W0max of the battery 31 continuously with time. When the treatment using the energy is continued (step S151—No), steps S148 to S150 are repeated with time. At and after the restart of the supply of the first driving electric power W1, the impedance Z1 is high, and the first driving electric power W1 is controlled under the constant voltage control. Thus, the first driving electric power W1 that is supplied is lower.

As described above, in the present modification as well as in the previously described embodiments and others, the sum of the first driving electric power W1 and the second driving electric power W2 that are supplied per unit time is kept less than or equal to the maximum source electric power W0max of the battery 31 continuously with time even in a state where both the first driving electric power W1 and the second driving electric power W2 are supplied. Thus, as in the previously described embodiments and others, the battery 31 which outputs low source electric power (electric capacity) W0 can be used in the energy treatment instrument 1.

In the present modification, at the start of the treatment, the first driving electric power W1 alone is first supplied, and the temperature of the treated target (living tissue) is raised to some degree by the high-frequency electric current I1. The second driving electric power W2 alone is then supplied at the maximum source electric power W0max, and the treated target is raised to the desired temperature (T0) by heat. The first driving electric power W1 and the second driving electric power W2 are controlled as described above, and the treated target (the heating element 65) can therefore be raised to the desired temperature T0 without the increase of the first driving electric power W1 (the high-frequency electric power P1) and the second driving electric power W2 (the heat generating electric power P'2).

Figure 18:
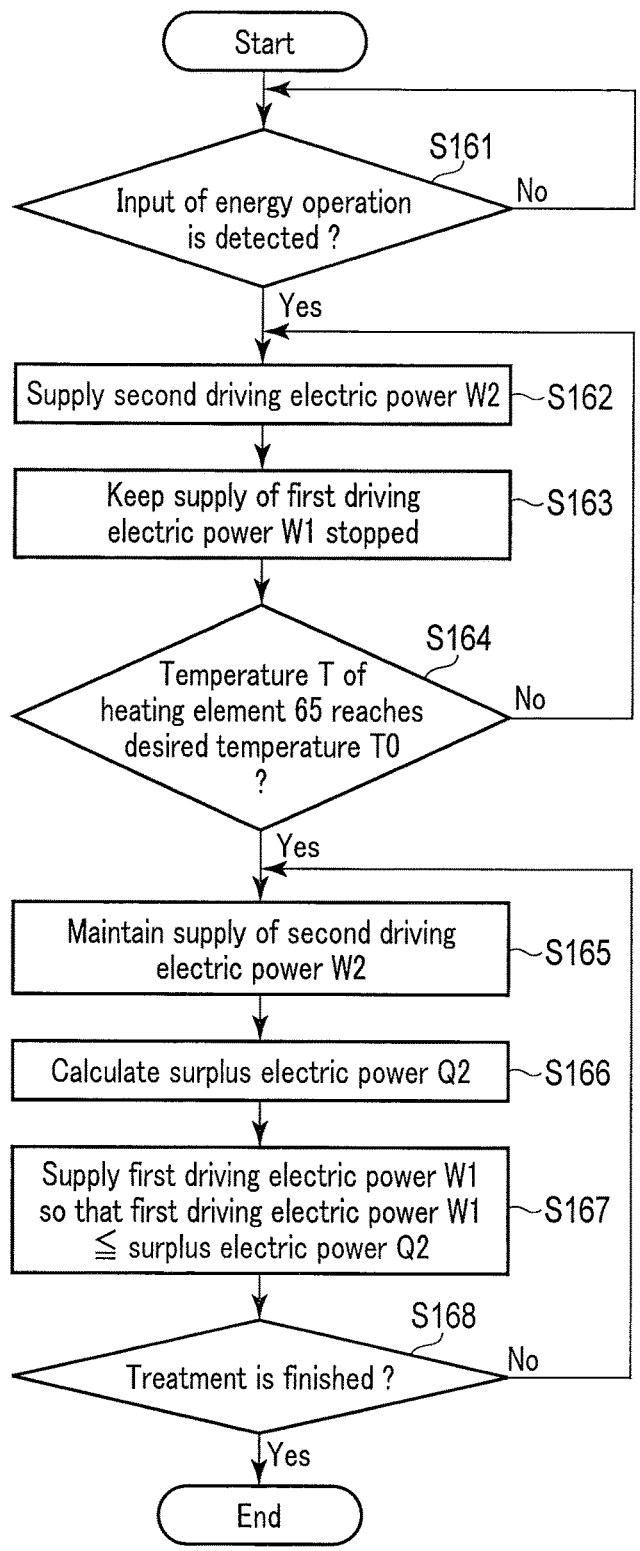
FIG. 18 is a flowchart showing processing in the energy treatment instrument in a state where the energy or the energies for use in the treatment is/are supplied to the treatment portion according to a third modification of the second embodiment.

Next, a third modification of the second embodiment shown in FIG. 18 and FIG. 19 is described. In the present modification as well, the prior energy setting section 36 is not provided, and the prior energy higher in priority is not set. FIG. 18 is a flowchart showing processing in the energy treatment instrument 1 in a state where the energy or the energies for use in the treatment is/are supplied to the treatment portion 10. FIG. 19 is a diagram showing changes of the first driving electric power W1 and the second driving electric power W2 with time in a state where the energy or the energies is/are supplied to the treatment portion 10. In FIG. 19, the time t is indicated on the abscissa axis, and the driving electric powers W (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

As shown in FIG. 18, in the present modification, when the operation input detector 45 detects the input of an energy operation (step S161—Yes), the controller 32 controls the driving state of the second energy generator 71 to supply the second driving electric power W2 to the second energy generator 71 (step S162). Accordingly, the heat generating electric power P'2 is supplied to the heating element 65, and the aforementioned treatment using the heat generated in the heating element 65 is conducted. In the present embodiment as well, the second driving electric power W2 is controlled on the basis of the temperature T of the heating element 65, and the constant electric power control to keep the electric power value of the second driving electric power W2 constant with time is performed until the temperature T reaches the desired temperature (set temperature) T0.

In the present modification, even if the supply of the second driving electric power W2 is started, the controller 32 controls the driving state of the first energy generator 41 to keep the supply of the first driving electric power W1 to the first energy generator 41 stopped (step S163). Therefore, at the start of the treatment with the treatment portion 10, the controller 32 starts the supply of the second driving electric power W2 to the second energy generator 71 without supplying the first driving electric power W1 to the first energy generator 41. In this instance, as shown in FIG. 19, the second driving electric power W2 is supplied in a state where the electric power value of the second driving electric power W2 is the same as the maximum source electric power W0max of the battery 31. However, the first driving electric power W1 is not supplied, so that as in the previously described embodiments and others, the sum of the first driving electric power W1 and the second driving electric power W2 that are supplied per unit time is kept less than or equal to the maximum source electric power W0max of the battery (actually, the same as the maximum source electric power W0max) continuously with time. In FIG. 19, the supply start time of the second driving electric power W2 is indicated by ts, and the supply stop time of the first driving electric power W1 and the second driving electric power W2 is indicated by te.

When a certain period of time passes in a state where the first driving electric power W1 is not supplied and the second driving electric power W2 alone is supplied, the temperature T of the heating element 65 reaches the desired temperature T0. Accordingly, the control of the second driving electric power W2 is switched to the constant temperature control to keep the temperature of the heating element 65 constant with time from the constant electric power control. That is, at and after the start of the supply of the second driving electric power W2, the supply state of the second driving electric power W2 is switched by the controller 32 from the constant electric power control to keep the second driving electric power W2 constant with time to the constant temperature control, in response to the fact that the temperature T has reached the desired temperature T0. Due to the switch to the constant temperature control, the electric power value of the second driving electric power W2 starts to decrease (from the maximum source electric power W0max in the present modification). When the temperature T does not reach the desired temperature T0 (step S164—No), steps S162 and S163 are repeated with time until the temperature T reaches the desired temperature T0 (i.e. until the control of the second driving electric power W2 is switched to the constant temperature control). In FIG. 19, at a time tk, the temperature T of the heating element 65 reaches the desired temperature T0, and the supply state of the second driving electric power W2 is switched from the constant electric power control to the constant temperature control.

When the temperature T of the heating element 65 reaches the desired temperature T0 (step S164—Yes), the controller 32 maintains the supply of the second driving electric power W2 (step S165), and the surplus electric power calculating section 37 calculates, with time, the surplus electric power (second surplus electric power) Q2 in which the second driving electric power W2 is subtracted from the maximum source electric power W0max of the battery 31 (step S166). The controller 32 then controls the driving state of the first energy generator 41 to supply the first driving electric power W1 to the first energy generator 41 (step S167). The supply of the first driving electric power W1 is started at the time of the switch of the supply state of the second driving electric power W2 to the constant temperature control (the time tk in FIG. 19) or immediately after the switch. That is, the supply of the first driving electric power W1 to the first energy generator 41 is started in response to the start of the decrease of the second driving electric power W2 resulting from the fact that the temperature T of the heating element 65 has reached the desired temperature T0.

In step S167, the first driving electric power W1 is supplied to the first energy generator 41 in a state where the first driving electric power W1 is less than or equal to the calculated surplus electric power Q2. That is, at and after the start of the supply of the first driving electric power W1, the controller 32 controls the first driving electric power W1 in a range in which the first driving electric power W1 is less than or equal to the surplus electric power Q2. Thus, the sum of the first driving electric power W1 and the second driving electric power W2 that are supplied per unit time is kept less than or equal to the maximum source electric power W0max of the battery 31 continuously with time. In this instance, the controller 32 adjusts the first driving electric power W1 by one of the constant current control, the constant electric power control, and the constant voltage control on the basis of the detection result of the impedance Z1 so that the first driving electric power W1 may be lower. However, at and after the supply start time tk of the first driving electric power W1, the temperature of the treated target is high due to the heat from the heating element 65, and the impedance (high-frequency impedance) Z1 is high. Thus, the first driving electric power W1 is mainly controlled under the constant voltage control, and the first driving electric power W1 does not increase. When the treatment using the energy is continued (step S168—No), steps S165 to S167 are repeated with time.

As described above, in the present modification as well as in the previously described embodiments and others, the sum of the first driving electric power W1 and the second driving electric power W2 that are supplied per unit time is kept less than or equal to the maximum source electric power W0max of the battery 31 continuously with time even in a state where both the first driving electric power W1 and the second driving electric power W2 are supplied. Thus, as in the previously described embodiments and others, the battery 31 which outputs low source electric power (electric capacity) W0 can be used in the energy treatment instrument 1.

Figure 20:
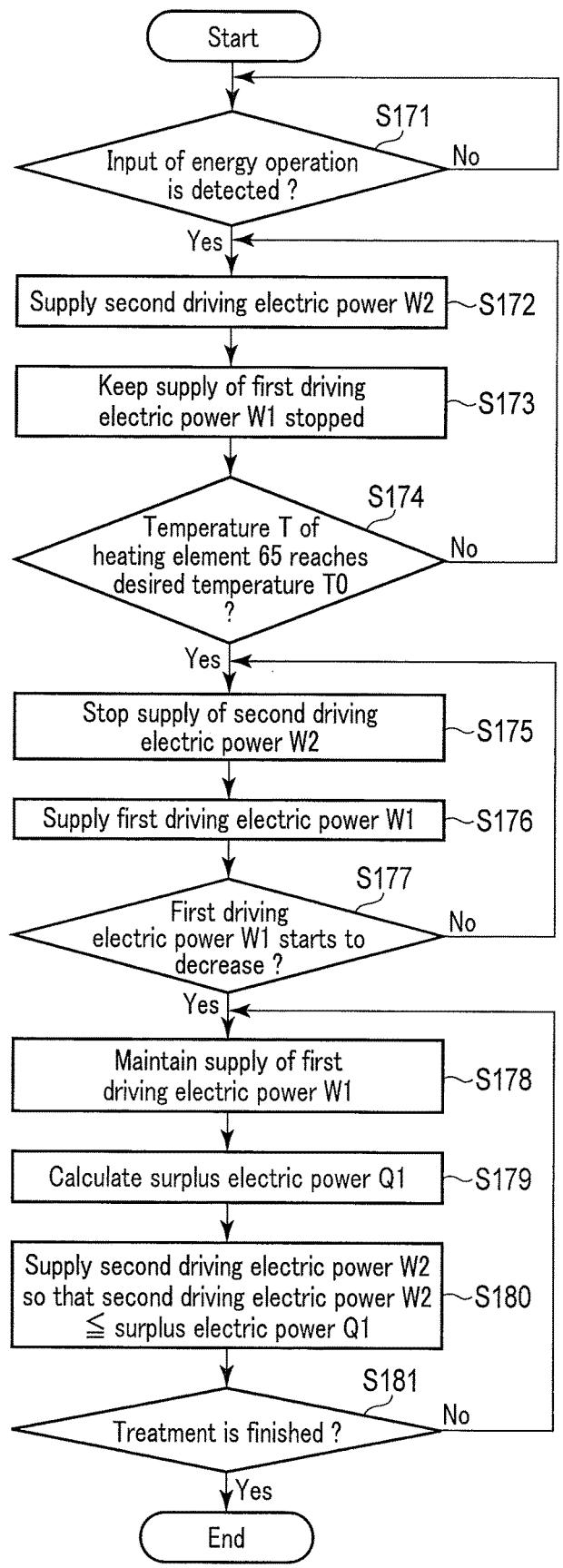
FIG. 20 is a flowchart showing processing in the energy treatment instrument in a state where the energy or the energies for use in the treatment is/are supplied to the treatment portion according to a fourth modification of the second embodiment.
Figure 21:
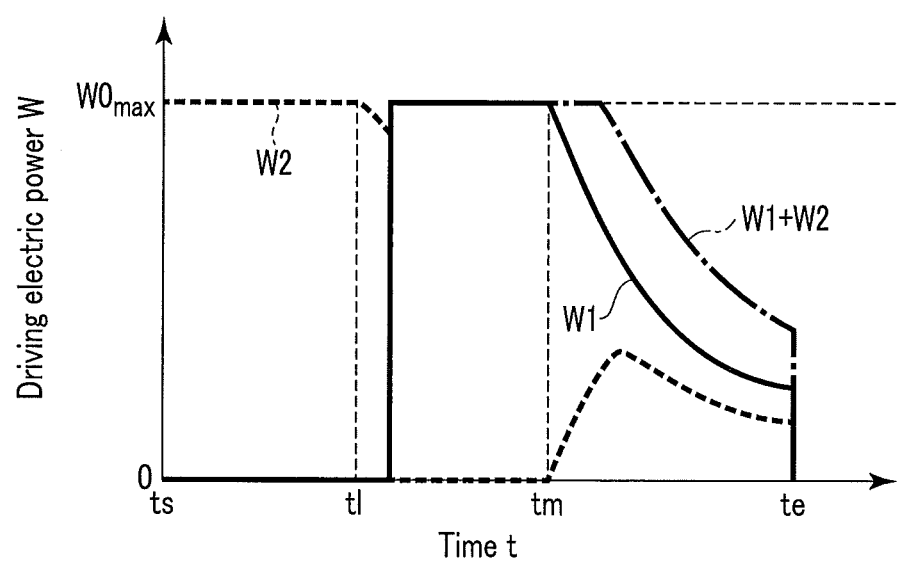
FIG. 21 is a schematic diagram showing changes of the first driving electric power and the second driving electric power with time in a state where the energy or the energies is/are supplied to the treatment portion according to the fourth modification of the second embodiment.

Next, a fourth modification of the second embodiment shown in FIG. 20 and FIG. 21 is described. In the present modification as well, the prior energy setting section 36 is not provided, and the prior energy higher in priority is not set. FIG. 20 is a flowchart showing processing in the energy treatment instrument 1 in a state where the energy or the energies for use in the treatment is/are supplied to the treatment portion 10. FIG. 21 is a diagram showing changes of the first driving electric power W1 and the second driving electric power W2 with time in a state where the energy or the energies is/are supplied to the treatment portion 10. In FIG. 21, the time t is indicated on the abscissa axis, and the driving electric powers W (W1 and W2) are indicated on the ordinate axis. The change of the first driving electric power W1 with time is indicated by a solid line, the change of the second driving electric power W2 with time is indicated by a broken line, and the change of the sum (W1+W2) of the first driving electric power W1 and the second driving electric power W2 with time is indicated by a dashed line.

As shown in FIG. 20, in the present modification as well as in the third modification of the second embodiment, when the operation input detector 45 detects the input of an energy operation (step S171—Yes), the controller 32 controls the driving state of the second energy generator 71 to supply the second driving electric power W2 to the second energy generator 71 (step S172). Accordingly, the heat generating electric power P'2 is supplied to the heating element 65, and the aforementioned treatment using the heat generated in the heating element 65 is conducted. In the present embodiment as well, the second driving electric power W2 is controlled on the basis of the temperature T of the heating element 65, and the constant electric power control to keep the electric power value of the second driving electric power W2 constant with time is performed until the temperature T reaches the desired temperature T0.

Even if the supply of the second driving electric power W2 is started, the controller 32 controls the driving state of the first energy generator 41 to keep the supply of the first driving electric power W1 to the first energy generator 41 stopped (step S173). Therefore, at the start of the treatment with the treatment portion 10, the controller 32 starts the supply of the second driving electric power W2 to the second energy generator 71 without supplying the first driving electric power W1 to the first energy generator 41. In this instance, as shown in FIG. 21, the second driving electric power W2 is supplied in a state where the electric power value of the second driving electric power W2 is the same as the maximum source electric power W0max of the battery 31. However, the first driving electric power W1 is not supplied, so that as in the previously described embodiments and others, the sum of the first driving electric power W1 and the second driving electric power W2 that are supplied per unit time is kept less than or equal to the maximum source electric power W0max of the battery 31 (actually, the same as the maximum source electric power W0max) continuously with time. In FIG. 21, the supply start time of the second driving electric power W2 is indicated by ts, and the supply stop time of the first driving electric power W1 and the second driving electric power W2 is indicated by te.

When a certain period of time passes in a state where the first driving electric power W1 is not supplied and the second driving electric power W2 alone is supplied, the temperature T of the heating element 65 reaches the desired temperature T0. Accordingly, the control of the second driving electric power W2 is switched to the constant temperature control to keep the temperature of the heating element 65 constant with time from the constant electric power control. That is, at and after the start of the supply of the second driving electric power W2, the supply state of the second driving electric power W2 is switched by the controller 32 from the constant electric power control to keep the second driving electric power W2 constant with time to the constant temperature control, in response to the fact that the temperature T has reached the desired temperature T0. Due to the switch to the constant temperature control, the electric power value of the second driving electric power W2 starts to decrease (from the maximum source electric power W0max in the present modification). When the temperature T does not reach the desired temperature T0 (step S174— No), steps S172 and S173 are repeated with time until the temperature T reaches the desired temperature T0 (i.e. until the control of the second driving electric power W2 is switched to the constant temperature control). In FIG. 21, at a time t1, the temperature T of the heating element 65 reaches the desired temperature T0, and the supply state of the second driving electric power W2 is switched from the constant electric power control to the constant temperature control.

When the temperature T of the heating element 65 reaches the desired temperature T0 (step S174—Yes), the controller 32 controls the driving state of the second energy generator 71 to stop the supply of the second driving electric power W2 to the second energy generator 71 (step S175). The controller 32 then controls the driving state of the first energy generator 41 to supply the first driving electric power W1 to the first energy generator 41 (step S176). The supply of the second driving electric power W2 to the second energy generator 71 is stopped and the supply of the first driving electric power W1 to the first energy generator 41 is started at the start of the decrease of the second driving electric power W2 (the time t1 in FIG. 21) or immediately after the start of the decrease. Therefore, at and after the start of the supply of the second driving electric power W2, the supply of the second driving electric power W2 to the second energy generator 71 is stopped and the supply of the first driving electric power W1 to the first energy generator 41 is started in response to the start of the decrease of the second driving electric power W2 resulting from the fact that the temperature T of the heating element 65 has reached the desired temperature T0.

In the present modification as well, the controller 32 adjusts the first driving electric power W1 by one of the constant current control, the constant electric power control, and the constant voltage control on the basis of the detection result of the impedance Z1 so that the first driving electric power W1 may be lower. As shown in FIG. 21, at the start of the supply of the first driving electric power W1 (immediately after the decrease start time t1 of the second driving electric power W2), the first driving electric power W1 is supplied under the constant electric power control to keep the first driving electric power W1 constant with time. For a certain period of time since the start of the supply the first driving electric power W1, the first driving electric power W1 is controlled under the constant electric power control, and the first driving electric power W1 is supplied in a state where the electric power value of the first driving electric power W1 is the same as the maximum source electric power W0max of the battery 31. In this instance, the second driving electric power W2 is not supplied, so that as in the previously described embodiments and others, the sum of the first driving electric power W1 and the second driving electric power W2 that are supplied per unit time is kept less than or equal to the maximum source electric power W0max of the battery 31 (actually, the same as the maximum source electric power W0max) continuously with time.

When a certain period of time passes since the start of the supply the first driving electric power W1, the impedance (high-frequency impedance) Z1 increases to a range in which the constant voltage control to keep the high-frequency voltage V1 constant with time is performed. That is, at and after the start of the supply of the first driving electric power W1, the supply state of the first driving electric power W1 is switched by the controller 32 from the constant electric power control to keep the first driving electric power W1 constant with time to the constant voltage control, in response to the change of the impedance Z1 for the high-frequency electric current I1 with time. Due to the switch to the constant voltage control, the electric power value of the first driving electric power W1 starts to decrease (from the maximum source electric power W0max in the present modification). When the first driving electric power W1 does not start to decrease (step S177—No), steps S175 and S176 are repeated with time until the first driving electric power W1 starts to decrease (i.e. until a switch to the constant voltage control is made). In FIG. 21, at a time tm, a switch is made from the constant electric power control to the constant voltage control, and the first driving electric power W1 starts to decrease.

When the first driving electric power W1 starts to decrease (step S177—Yes), the controller 32 maintains the supply of the first driving electric power W1 (step S178), and the surplus electric power calculating section 37 calculates, with time, the surplus electric power (first surplus electric power) Q1 in which the first driving electric power W1 is subtracted from the maximum source electric power W0max of the battery 31 (step S179). The controller 32 then controls the driving state of the second energy generator 71 to supply the second driving electric power W2 to the second energy generator 71 (step S180). The supply of the second driving electric power W2 is started at the start of the decrease of the first driving electric power W1 (the time tm in FIG. 21) or immediately after the start of the decrease. That is, the supply of the second driving electric power W2 to the second energy generator 71 is restarted in response to the start of the decrease of the first driving electric power W1.

In step S180, the second driving electric power W2 is supplied to the second energy generator 71 in a state where the second driving electric power W2 is less than or equal to the calculated surplus electric power Q1. That is, at and after the restart of the supply of the second driving electric power W2, the controller 32 controls the second driving electric power W2 in a range in which the second driving electric power W2 is less than or equal to the surplus electric power Q1. Thus, the sum of the first driving electric power W1 and the second driving electric power W2 that are supplied per unit time is kept less than or equal to the maximum source electric power W0max of the battery 31 continuously with time. When the treatment using the energy is continued (step S181—No), steps S178 to S180 are repeated with time. At and after the restart of the supply of the second driving electric power W2, the temperature T of the treated target (the heating element 65) is high, and the second driving electric power W2 is mainly controlled under the constant temperature control. Thus, the second driving electric power W2 that is supplied is lower.

As described above, in the present modification as well as in the previously described embodiments and others, the sum of the first driving electric power W1 and the second driving electric power W2 that are supplied per unit time is kept less than or equal to the maximum source electric power W0max of the battery 31 continuously with time even in a state where both the first driving electric power W1 and the second driving electric power W2 are supplied. Thus, as in the previously described embodiments and others, the battery 31 which outputs low source electric power (electric capacity) W0 can be used in the energy treatment instrument 1.

Other Modifications

In the previously described embodiments and others, the high-frequency electric power P1 is supplied to the treatment portion 10 as the first energy, and the ultrasonic vibration or heat is supplied to the treatment portion 10 as the second energy, but it is not limited thereto. It is only necessary to be able to simultaneously supply the treatment portion (10) with the first energy and the second energy which is different in characteristics for a treatment from the first energy.

Although the battery 31 is provided as the electric power source in the previously described embodiments and others, it is not limited thereto. For example, the holding unit 2 may be connected to an energy source unit (not shown) such as an energy generator via an unshown cable (universal cord), and the electric power source (31), the first energy generator (41) which generates the first energy, and the second energy generator (51 or 71) which generates the second energy may be provided in the energy source unit. In this case as well, the maximum source electric power (W0max) which is the maximum value of the source electric power (W0) output from the electric power source (31) per unit time is defined, for example, at the time of manufacture.

In the previously described embodiments and others, the treated target is grasped between two grasping members (between the probe distal portion 21 and the jaw 18 or between the first jaw 62 and the second jaw 63), but it is not limited thereto. For example, the treatment portion (10) may be formed into the shape of a hook, and the treated target may be caught on the hook to conduct a treatment to resect the treated target. In this case, the high-frequency electric power (P1) is supplied to the treatment portion (10) as the first energy, and the ultrasonic vibration is transmitted to the treatment portion (10) as the second energy.

In the previously described embodiments and others, the energy treatment instrument (1) includes the electric power source (31) in which the maximum source electric power (W0max) that is the maximum value of the source electric power (W0) output per unit time is defined, the first energy generator (41) which generates the first energy by the supply of the first driving electric power (W1) resulting from the source electric power (W0) output from the electric power source (31), and the second energy generator (51; 71) which generates the second energy by the supply of the second driving electric power (W2) resulting from the source electric power (W0) output from the electric power source (31). The treatment portion (10) can conduct a treatment by simultaneously using the first energy and the second energy, and the electric power detector (42, 52; 42, 72) detects, with time, the first driving electric power (W1) supplied to the first energy generator (41) and the second driving electric power (W2) supplied to the second energy generator (51; 71). The controller (32) controls the first energy generator (41) and the second energy generator (51; 71) on the basis of a detection result in the electric power detector (42, 52; 42, 72) to keep the sum (W1+W2) of the first driving electric power (W1) and the second driving electric power (W2) that are supplied per unit time less than or equal to the maximum source electric power (W0max) of the electric power source (31) continuously with time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment apparatus comprising:
   an electric power source in which maximum source electric power that is a maximum value of source electric power output per unit time is defined;
   a first energy generator to which first driving electric power is supplied due to the source electric power, and which is driven by the first driving electric power to generate first energy;
   a second energy generator to which second driving electric power is supplied due to the source electric power, and which is driven by the second driving electric power to generate second energy different from the first energy;
   a treatment portion configured to conduct a treatment by simultaneously using the first energy and the second energy;
   an electric power detector configured to detect the first driving electric power and the second driving electric power with time;
   a controller which is configured to control the first energy generator and the second energy generator on the basis of a detection result in the electric power detector to keep the sum of the first driving electric power and the second driving electric power that are supplied per unit time less than or equal to the maximum source electric power of the electric power source continuously with time; and
   a prior energy setting section which is configured to set one of the first energy and the second energy that is higher in priority in the treatment with the treatment portion,
   wherein when the prior energy setting section sets that the priority of the first energy is higher, the controller is configured to keep, continuously with time, the second driving electric power less than or equal to first surplus electric power in which the first driving electric power is subtracted from the maximum source electric power.

2. The energy treatment apparatus according to claim 1, wherein when a maximum value of the first driving electric power supplied per unit time is first maximum driving electric power and when a maximum value of the second driving electric power supplied per unit time is second maximum driving electric power, the maximum source electric power of the battery is lower than the sum of the first maximum driving electric power and the second maximum driving electric power.

3. The energy treatment apparatus according to claim 2, wherein each of the first maximum driving electric power and the second maximum driving electric power is less than or equal to the maximum source electric power of the electric power source.

4. The energy treatment apparatus according to claim 1, wherein
   when the prior energy setting section sets that the priority of the second energy is higher, the controller is configured to keep, continuously with time, the first driving electric power less than or equal to second surplus electric power in which the second driving electric power is subtracted from the maximum source electric power.

5. The energy treatment apparatus according to claim 1, further comprising:
   a power source observing section configured to observe the electric power source with time; and
   a maximum electric power updating section configured to update the defined maximum source electric power of the electric power source on the basis of an observation result in the power source observing section,
   wherein when the maximum source electric power defined by the maximum electric power updating section is updated, the controller is configured to keep, continuously with time, the sum of the first driving electric power and the second driving electric power that are supplied per unit time less than or equal to the updated maximum source electric power of the electric power source.

6. The energy treatment apparatus according to claim 1, further comprising:
   electrode portions which are provided in the treatment portion, and which are supplied with high-frequency electric power generated as the first energy in the first energy generator and thereby function as electrodes of the high-frequency electric power; and
   a heating element which is configured to generate heat when supplied with heat generating electric power generated as the second energy in the second energy generator, and configured to transmit the generated heat to the treatment portion as the second energy.

7. The energy treatment apparatus according to claim 6, further comprising:
   an impedance detector configured to detect, with time, impedance for a high-frequency electric current flowing between the electrode portions; and
   a temperature detector configured to detect a temperature of the heating element with time.

8. The energy treatment apparatus according to claim 7, wherein at the start of the treatment with the treatment portion, the controller is configured to start the supply of the first driving electric power to the first energy generator in a state where the supply of the second driving electric power to the second energy generator is stopped,
   at and after the start of the supply of the first driving electric power, the controller is configured to switch the supply state of the first driving electric power in response to the change of the impedance for the high-frequency electric current with time from constant electric power control to keep the first driving electric power constant with time to constant voltage control to keep a voltage applied by the supply of the first driving electric power constant with time, and
   the controller is configured to start the supply of the second driving electric power to the second energy generator in response to the switch of the supply state of the first driving electric power to the constant voltage control, and at and after the start of the supply of the second driving electric power, the controller is configured to keep, continuously with time, the second driving electric power less than or equal to surplus electric power in which the first driving electric power is subtracted from the maximum source electric power.

9. The energy treatment apparatus according to claim 7, wherein at the start of the treatment with the treatment portion, the controller is configured to start the supply of the first driving electric power to the first energy generator in a state where the supply of the second driving electric power to the second energy generator is stopped, at and after the start of the supply of the first driving electric power, the controller is configured to stop the supply of the first driving electric power to the first energy generator and configured to start the supply of the second driving electric power to the second energy generator in response to the start of the decrease of the first driving electric power resulting from the change of the impedance for the high-frequency electric current with time, at and after the start of the supply of the second driving electric power, the controller is configured to switch the supply state of the second driving electric power in response to the change of the temperature of the heating element with time from constant electric power control to keep the second driving electric power constant with time to constant temperature control to keep the temperature of the heating element constant with time, and the controller is configured to restart the supply of the first driving electric power to the first energy generator in response to the switch of the supply state of the second driving electric power to the constant temperature control, and at and after the restart of the supply of the first driving electric power, the controller is configured to keep, continuously with time, the first driving electric power less than or equal to surplus electric power in which the second driving electric power is subtracted from the maximum source electric power.

10. The energy treatment apparatus according to claim 7, wherein at the start of the treatment with the treatment portion, the controller is configured to start the supply of the second driving electric power to the second energy generator in a state where the supply of the first driving electric power to the first energy generator is stopped, and at and after the start of the supply of the second driving electric power, the controller is configured to start the supply of the first driving electric power to the first energy generator in response to the start of the decrease of the second driving electric power resulting from the fact that the temperature of the heating element has reached a set temperature, and at and after the start of the supply of the first driving electric power, the controller is configured to keep, continuously with time, the first driving electric power less than or equal to surplus electric power in which the second driving electric power is subtracted from the maximum source electric power.

11. The energy treatment apparatus according to claim 7, wherein at the start of the treatment with the treatment portion, the controller is configured to start the supply of the second driving electric power to the second energy generator in a state where the supply of the first driving electric power to the first energy generator is stopped, at and after the start of the supply of the second driving electric power, the controller is configured to stop the supply of the second driving electric power to the second energy generator and configured to start the supply of the first driving electric power to the first energy generator in response to the start of the decrease of the second driving electric power resulting from fact that the temperature of the heating element has reached a set temperature, and the controller is configured to restart the supply of the second driving electric power to the second energy generator in response to the start of the decrease of the first driving electric power resulting from the change of the impedance for the high-frequency electric current with time, and at and after the restart of the supply of the second driving electric power, the controller is configured to keep, continuously with time, the second driving electric power less than or equal to surplus electric power in which the first driving electric power is subtracted from the maximum source electric power.

12. The energy treatment apparatus according to claim 1, further comprising:

electrode portions which are provided in the treatment portion, and which are supplied with high-frequency electric power generated as the first energy in the first energy generator and thereby function as electrodes of the high-frequency electric power; and a vibration generator which is configured to generate an ultrasonic vibration when supplied with vibration generating electric power generated as the second energy in the second energy generator, and configured to transmit the generated ultrasonic vibration to the treatment portion as the second energy.

13. The energy treatment apparatus according to claim 12, further comprising an impedance detector configured to detect, with time, impedance for a high-frequency electric current flowing between the electrode portions.

14. The energy treatment apparatus according to claim 13, wherein at the start of the treatment with the treatment portion, the controller is configured to start the supply of the first driving electric power to the first energy generator in a state where the supply of the second driving electric power to the second energy generator is stopped, at and after the start of the supply of the first driving electric power, the controller is configured to switch the supply state of the first driving electric power in response to the change of the impedance for the high-frequency electric current with time from constant electric power control to keep the first driving electric power constant with time to constant voltage control to keep a voltage applied by the supply of the first driving electric power constant with time, and the controller is configured to start the supply of the second driving electric power to the second energy generator in response to the switch of the supply state of the first driving electric power to the constant voltage control, and at and after the start of the supply of the second driving electric power, the controller is configured to keep, continuously with time, the second driving electric power less than or equal to surplus electric power in which the first driving electric power is subtracted from the maximum source electric power.

15. The energy treatment apparatus according to claim 1, further comprising a holding unit configured to be held, wherein the electric power source includes a battery which is attached to the holding unit.

* * * * *